United States Patent
Buffa et al.

(10) Patent No.: US 10,618,984 B2
(45) Date of Patent: Apr. 14, 2020

(54) UNSATURATED DERIVATIVES OF POLYSACCHARIDES, METHOD OF PREPARATION THEREOF AND USE THEREOF

(71) Applicant: Contipro a.s., Dolni Dobrouc (CZ)

(72) Inventors: Radovan Buffa, Humenne (SK); Tomas Bobula, Svit (SK); Petra Sedova, Ceska Trebova (CZ); Ivana Basarabova, Medzilaborce (SK); Pavlina Prochazkova, Vlkos (CZ); Hana Vagnerova, Dolni Cermna (CZ); Iva Doleckova, Hradec Kralove (CZ); Sona Moravcikova, Jamne nad Orlici (CZ); Vladimir Velebny, Zamberk (CZ)

(73) Assignee: Contipro a.s., Dolni Dobrouc (CZ)

( * ) Notice: Subject to any disclaimer, the term of this patent is extended or adjusted under 35 U.S.C. 154(b) by 0 days.

(21) Appl. No.: 16/311,745

(22) PCT Filed: Jun. 26, 2017

(86) PCT No.: PCT/CZ2017/050026
§ 371 (c)(1),
(2) Date: Dec. 20, 2018

(87) PCT Pub. No.: WO2018/001394
PCT Pub. Date: Jan. 4, 2018

(65) Prior Publication Data
US 2019/0169317 A1    Jun. 6, 2019

(30) Foreign Application Priority Data
Jun. 27, 2016    (CZ) .............................. PV 2016-375

(51) Int. Cl.
| C08B 37/08 | (2006.01) |
| C08B 37/00 | (2006.01) |
| A61K 31/728 | (2006.01) |
| A61K 31/731 | (2006.01) |
| A61K 31/737 | (2006.01) |
| A61K 31/726 | (2006.01) |

(52) U.S. Cl.
CPC ........ *C08B 37/0072* (2013.01); *A61K 31/726* (2013.01); *A61K 31/728* (2013.01); *A61K 31/731* (2013.01); *A61K 31/737* (2013.01); *C08B 37/00* (2013.01); *C08B 37/0042* (2013.01); *C08B 37/0069* (2013.01)

(58) Field of Classification Search
None
See application file for complete search history.

(56) References Cited

U.S. PATENT DOCUMENTS

| 3,075,527 A | 1/1963 | Bechtold |
| 3,720,662 A | 3/1973 | Tessler et al. |
| 3,728,223 A | 4/1973 | Kaneko et al. |
| 4,043,331 A | 8/1977 | Martin et al. |
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,462,976 A | 10/1995 | Matsuda et al. |
| 5,520,916 A | 5/1996 | Dorigatti et al. |
| 5,522,879 A | 6/1996 | Scopelianos |
| 5,550,225 A | 8/1996 | Philippe |
| 5,616,568 A | 4/1997 | Pouyani et al. |

(Continued)

FOREIGN PATENT DOCUMENTS

| CA | 2512730 A1 | 7/2004 |
| CH | 628088 A5 | 2/1982 |

(Continued)

OTHER PUBLICATIONS

Werner, T. et al., "Simple Method for the Preparation of Esters from Grignard Reagents and Alkyl 1-Imidazolecarboxylates," J. Org. Chem. (2006) 71(11):4302-4304.

Won, K. et al., "Horseradish Peroxidase-Catalyzed Polymerization of Cardanol in the Presence of Redox Mediators,"Biomacromolecules (2003) 5(1), 1-4.

Wondraczek, H. et al., "Synthesis of highly functionalized dextran alkyl carbonates showing nanosphere formation," Carbohydrate Polymers (2011) 83:1112-1118.

Written Opinion in International Patent Application No. PCT/CZ2009/000131, dated Apr. 9, 2010, 3 pgs.

(Continued)

*Primary Examiner* — Layla D Berry (74) *Attorney, Agent, or Firm* — Wood Herron & Evans LLP (57) ABSTRACT

The invention relates to the preparation of new polysaccharide derivatives comprising a double bond in the positions 4 and 5 of the pyranose cycle. The method of preparation consists in the oxidation of OH group in the position 6 to an aldehyde, followed by the elimination to form a double —C═C— bond in the positions 4 and 5, and the final reduction of the aldehyde group in the position 6 into the original alcohol. The derivatives of polysaccharides prepared according to the invention show an enhanced antioxidant activity and some of them also a selective negative influence on carcinoma cell viability. (formula) where R represents —NH—CO—CH$_3$ or —OH.

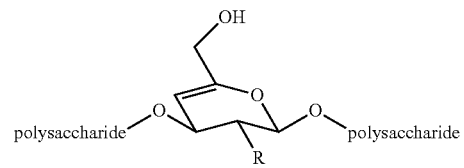

15 Claims, 1 Drawing Sheet

(56) References Cited

U.S. PATENT DOCUMENTS

| | | |
|---|---|---|
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,162,537 A | 12/2000 | Martin et al. |
| 6,207,134 B1 | 3/2001 | Fahlvik et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,641,798 B2 | 11/2003 | Achilefu et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,125,860 B1 | 10/2006 | Renier et al. |
| 7,214,759 B2 | 5/2007 | Pacetti et al. |
| 7,345,117 B1 | 3/2008 | Barbucci et al. |
| 7,550,136 B2 | 6/2009 | Warner et al. |
| 7,680,038 B1 | 3/2010 | Gourlay |
| 7,951,936 B2 | 5/2011 | Sato |
| 8,062,654 B2 | 11/2011 | Nelson et al. |
| 8,129,449 B2 | 3/2012 | Heinzman et al. |
| 8,143,391 B2 | 3/2012 | Yasugi et al. |
| 8,247,546 B2 | 8/2012 | Stucchi et al. |
| 9,017,725 B2 | 4/2015 | Mitra et al. |
| 9,492,586 B2 | 11/2016 | Wolfova et al. |
| 9,522,966 B2 | 12/2016 | Buffa et al. |
| 2002/0016472 A1 | 2/2002 | Tsien et al. |
| 2002/0026039 A1 | 2/2002 | Bellini et al. |
| 2002/0076810 A1 | 6/2002 | Radice et al. |
| 2003/0113354 A1 | 6/2003 | Schmid et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0112349 A1 | 5/2005 | Laurencin et al. |
| 2005/0118231 A1 | 6/2005 | El Meski et al. |
| 2005/0119219 A1 | 6/2005 | Bellini et al. |
| 2005/0126338 A1 | 6/2005 | Yadav |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0188578 A1 | 8/2006 | Fernandez et al. |
| 2006/0189516 A1 | 8/2006 | Yang et al. |
| 2006/0216324 A1 | 9/2006 | Stucke et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0009630 A1 | 1/2008 | Gao et al. |
| 2008/0063617 A1 | 3/2008 | Abrahams et al. |
| 2008/0071001 A1 | 3/2008 | Sato |
| 2008/0124395 A1 | 5/2008 | Chen et al. |
| 2008/0286300 A1 | 11/2008 | Bardotti et al. |
| 2009/0024019 A1 | 1/2009 | Stein et al. |
| 2009/0028788 A1 | 1/2009 | Achilefu |
| 2009/0180966 A1 | 7/2009 | Borbely et al. |
| 2009/0252810 A1 | 10/2009 | Tommeraas et al. |
| 2010/0002155 A1 | 1/2010 | Yamaguchi et al. |
| 2010/0172892 A1 | 7/2010 | Uvarkina et al. |
| 2010/0207078 A1 | 8/2010 | Marder et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0020917 A1 | 1/2011 | Wen et al. |
| 2011/0028062 A1 | 2/2011 | Chester et al. |
| 2011/0104070 A1 | 5/2011 | Kang et al. |
| 2011/0111012 A1 | 5/2011 | Pepper et al. |
| 2011/0196328 A1 | 8/2011 | Bellini et al. |
| 2011/0200676 A1 | 8/2011 | Lin et al. |
| 2011/0218331 A1 | 9/2011 | Buffa et al. |
| 2011/0229551 A1 | 9/2011 | Doshi et al. |
| 2011/0263724 A1 | 10/2011 | Gurtner et al. |
| 2012/0040463 A1 | 2/2012 | Domard et al. |
| 2012/0095205 A1 | 4/2012 | Buffa et al. |
| 2012/0245323 A1 | 9/2012 | Buffa et al. |
| 2012/0264913 A1 | 10/2012 | Buffa et al. |
| 2012/0277416 A1 | 11/2012 | Carter et al. |
| 2012/0289478 A1 | 11/2012 | Rovati |
| 2013/0017367 A1 | 1/2013 | Ravagnan et al. |
| 2013/0136784 A1 | 5/2013 | Staab |
| 2013/0195791 A1 | 8/2013 | Berkland et al. |
| 2013/0309706 A1 | 11/2013 | Kruglick |
| 2014/0120069 A1 | 5/2014 | Huerta-Angeles et al. |
| 2014/0242145 A1 | 8/2014 | Yoo et al. |
| 2015/0157463 A1 | 6/2015 | Stad et al. |
| 2015/0320873 A1 | 11/2015 | Smejkalova et al. |

FOREIGN PATENT DOCUMENTS

| | | |
|---|---|---|
| CN | 101897976 A | 12/2010 |
| CN | 102154738 A | 8/2011 |
| CN | 103505736 A | 1/2014 |
| CN | 103789874 A | 5/2014 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 303879 B6 | 6/2013 |
| CZ | 304072 B6 | 9/2013 |
| CZ | 304266 B6 | 2/2014 |
| CZ | 304303 B6 | 2/2014 |
| CZ | 20120537 A3 | 3/2014 |
| CZ | 304512 B6 | 6/2014 |
| CZ | 305153 B6 | 5/2015 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| EP | 2522337 A2 | 11/2012 |
| EP | 2899214 A1 | 7/2015 |
| JP | 62104579 A | 5/1987 |
| JP | 63044883 A | 11/1988 |
| JP | H0214019 A | 1/1990 |
| JP | H0347801 A | 2/1991 |
| JP | 06025306 A | 2/1994 |
| JP | H0625306 A | 2/1994 |
| JP | 3308742 B2 | 7/2002 |
| JP | 2004507586 A | 3/2004 |
| JP | 2004123785 A | 4/2004 |
| JP | 2007262595 A | 10/2007 |
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| KR | 20080111815 A | 12/2008 |
| KR | 20120118681 A | 10/2012 |
| KR | 20130085294 A | 7/2013 |
| NL | 9700003 A | 7/1997 |
| WO | 9311803 A1 | 6/1993 |
| WO | 9627615 A1 | 9/1996 |
| WO | 9635720 A1 | 11/1996 |
| WO | 9637519 A1 | 11/1996 |

(56) References Cited

FOREIGN PATENT DOCUMENTS

| | | |
|---|---|---|
| WO | 9808876 A1 | 3/1998 |
| WO | 9901143 A1 | 1/1999 |
| WO | 9957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 2002032285 A2 | 4/2002 |
| WO | 0248197 A1 | 6/2002 |
| WO | 02057210 A1 | 7/2002 |
| WO | 2004061171 A2 | 7/2004 |
| WO | 2005028632 A2 | 3/2005 |
| WO | 2005092390 A2 | 10/2005 |
| WO | 2005092929 A1 | 10/2005 |
| WO | 2006010066 A2 | 1/2006 |
| WO | 2006026104 A2 | 3/2006 |
| WO | 2006056204 A1 | 6/2006 |
| WO | 2006102374 A2 | 9/2006 |
| WO | 2007003905 A1 | 1/2007 |
| WO | 2007006403 A2 | 1/2007 |
| WO | 2007009728 A1 | 1/2007 |
| WO | 2007033677 A1 | 3/2007 |
| WO | 2007101243 A1 | 9/2007 |
| WO | 2008014787 A1 | 2/2008 |
| WO | 2008031525 A1 | 3/2008 |
| WO | 2008077172 A2 | 7/2008 |
| WO | 2008115799 A1 | 9/2008 |
| WO | 2009037566 A2 | 3/2009 |
| WO | 2009050389 A2 | 4/2009 |
| WO | 2009108100 A1 | 9/2009 |
| WO | 2009148405 A1 | 12/2009 |
| WO | 2010018324 A1 | 2/2010 |
| WO | 2010028025 A1 | 3/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010105582 A1 | 9/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |
| WO | 2011069475 A2 | 6/2011 |
| WO | 2012034544 A2 | 3/2012 |
| WO | 2012089179 A1 | 7/2012 |
| WO | 2012146218 A1 | 11/2012 |
| WO | 2013056312 A1 | 4/2013 |
| WO | 2013159757 A1 | 10/2013 |
| WO | 2013167098 A2 | 11/2013 |
| WO | 2013171764 A2 | 11/2013 |
| WO | 2014023272 A1 | 2/2014 |
| WO | 2014082608 A1 | 6/2014 |
| WO | 2014082609 A1 | 6/2014 |
| WO | 2014082611 A1 | 6/2014 |

OTHER PUBLICATIONS

Written Opinion in International Patent Application No. PCT/CZ2010/000030, dated Sep. 1, 2010, 4 pgs.
Written Opinion in International Patent Application No. PCT/CZ2010/000128, dated Jun. 9, 2011, 4 pgs.
Written Opinion in International Patent Application No. PCT/CZ2010/000129, dated Jun. 15, 2011, 4 pgs.
Written Opinion in International Patent Application No. PCT/CZ2011/000126, dated Apr. 12, 2012, 4 pgs.
Written Opinion in International Patent Application No. PCT/CZ2012/000035, dated Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000057, dated Jul. 24, 2013, 4 pgs.
Written Opinion in International Patent Application No. PCT/CZ2013/000063, dated Apr. 23, 2015, 9 pgs.
Written Opinion in International Patent Application No. PCT/CZ2013/000091, dated Oct. 31, 2013, 4 pgs.
Written Opinion in International Patent Application No. PCT/CZ2013/000116, dated Jan. 28, 2014, 5 pgs.
Written Opinion in International Patent Application No. PCT/CZ2013/000155, dated Feb. 19, 2014, 6 pgs.
Written Opinion in International Patent Application No. PCT/CZ2013/000156, dated Apr. 4, 2014, 7 pgs.
Written Opinion in International Patent Application No. PCT/CZ2013/000157, dated Mar. 19, 2014, 6 pgs.
Written Opinion in International Patent Application No. PCT/CZ2013/000158, dated Mar. 19, 2014, 7 pgs.
Written Opinion in International Patent Application No. PCT/CZ2014/000138, dated May 4, 2015, 5 pgs.
Written Opinion in International Patent Application No. PCT/CZ2015/000018, dated Jul. 22, 2015, 8 pgs.
Written Opinion in International Patent Application No. PCT/CZ2015/000068, dated Jan. 8, 2016, 6 pgs.
Written Opinion in International Patent Application No. PCT/CZ2016/000027, dated Jun. 27, 2016, 6 pgs.
Written Opinion in International Patent Application No. PCT/CZ2016/000065, dated Sep. 30, 2016, 5 pgs.
Written Opinion in International Patent Application No. PCT/CZ2016/000071, dated Oct. 10, 2016, 5 pgs.
Written Opinion in International Patent Application No. PCT/CZ2016/050036, dated Feb. 6, 2017, 6 pgs.
Written Opinion in International Patent Application No. PCT/CZ2016/050048, dated May 3, 2017, 6 pgs.
Written Opinion in International Patent Application No. PCT/CZ2017/050026, dated Oct. 26, 2017, 5 pgs.
Written Opinion in International Patent Application No. PCT/EP2016/064653, dated Aug. 25, 2016, 6 pgs.
Xu, Y. et al., "Feasibility study of a novel crosslinking reagent (alginate dialdehyde) for biological tissue fixation," Carbohydrate Polymers (2012) 87(2):1589-1595.
Xu, Y.-P. et al., "Kinetics of Phenolic Polymerization Catalyzed by Peroxidase in Organic Media," Biotechnology and Bioengineering (1995) 47(1):117-119.
Yamane, Shintaro et al., "Feasibility of chitosan-based hyaluronic acid hybrid biomaterial for a novel scaffold in cartilage tissue engineering," Biomaterials (2005) 26(6);611-619.
Yang, Rui-Meng et al., "Hylauronan-modified superparamagnetic iron oxide nanoparticles for bimodal breast cancer imaging and photothermal therapy," Int'l J. of Nanomedicine 2017: 12, pp. 197-206.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Ye, Y. et al., "Integrin Targeting for Tumor Optical Imaging," Theranostics 2011, 1, 102-126.
Ye, Y. et al., "Multivalent Carbocyanine Molecular Probes: Synthesis and Applications," Bioconjugate Chem. 2005, 16, 51-61.
Ye, Y. et al., "Novel Near-Infrared Fluorescent Integrin-Targeted DFO Analogue," Bioconjugate Chem. (2008) 19:225-234.
Ye, Y. et al., "Polyvalent Carbocyanine Molecular Beacons for Molecular Recognitions," J. Am. Chem. Soc. 2004, 126, 7740-7741.
Yeom, J. et al., "Effect of Cross-Linking Reagents for Hyaluronic Acid Hydrogel Dermal Fillers on Tissue Augmentation and Regeneration," Bioconjugate Chemistry (2010) 21(2):240-247.
Zaafarany, I. et al., "Oxidation of Some Sulfated Carbohydrates: Kinetics and Mechanism of Oxidation of Chondroitin-4-Sulfate by Alkaline Permanganate with Novel Synthesis of Coordination Biopolymer Precursor," J. Mat. Sci. Res. (2013) 2(4):23-36.
Zeng, J. et al., "Photo-Induced Solid-State Crosslinking of Electrspun Poly(vinyl alcohol) Fibers," Macromolecular Rapid Communications (2005) 26:1557-1562.
Zeng, Yuan-Xian et al., "Preparation and Enhancement of Thermal Conductivity of Heat Transfer Oil-Based MoS2 Nanofluids," Journal of Nanomaterials, vol. 2013, Art. ID 270490, 6 pgs.

(56) References Cited

OTHER PUBLICATIONS

Zhong, S.P. et al., "Biodegradation of hyaluronic acid derivatives by hyalurondiase," Biomaterials (1994) 15 (5):359-365.
Zou, X.H. et al., "Specific interactions between human fibroblasts and particular chondroitin sulfate molecules for wound healing," Acta Biomaterialia (2009) 5(5):1588-1595.
Mondek, J. et al., "Thermal degradation of high molar mass hyaluronan in solution and in powder; comparison with BSA," Polymer Degradation and Stability (2015) 120:107-113.
Nevell, T.P. et al., "Cellulose Chemistry and its Applications," 1985, John Wiley & Sons, pp. 455-479.
Nimmo, C. M. et al., "Diels-Alder Click Cross-Linked Hyaluronic Acid Hydrogels for Tissue Engineering," Biomacromolecules (2011) 12:824-830.
Normandin, L. et al., "Manganese Neurotoxicity: An Update of Pathophysiologic Mechanisms," Metab Brain Dis (2002)17(4):375-387.
Office Action in U.S. Appl. No. 13/512,484, dated May 11, 2016, 8 pgs.
Office Action in U.S. Appl. No. 13/512,484, dated Oct. 1, 2015, 8 pgs.
Office Action in U.S. Appl. No. 13/512,484, dated Sep. 11, 2014, 8 pgs.
Office Action in U.S. Appl. No. 13/514,759, dated Jul. 30, 2015, 12 pgs.
Office Action in U.S. Appl. No. 13/514,759, dated Sep. 24, 2014, 10 pgs.
Office Action in U.S. Appl. No. 13/977,181, dated Jan. 22, 2016, 8 pgs.
Office Action in U.S. Appl. No. 14/113,527, dated Feb. 12, 2016, 11 pgs.
Office Action in U.S. Appl. No. 14/113,527, dated Sep. 8, 2016, 10 pgs.
Office Action in U.S. Appl. No. 14/395,575, dated Jul. 6, 2017, 9 pgs.
Office Action in U.S. Appl. No. 14/420,012, dated Jun. 16, 2016, 6 pgs.
Office Action in U.S. Appl. No. 14/430,731, dated May 19, 2016, 12 pgs.
Office Action in U.S. Appl. No. 14/647,185, dated Sep. 28, 2016, 5 pgs.
Office Action in U.S. Appl. No. 14/647,626, dated Feb. 17, 2017, 12 pgs.
Office Action in U.S. Appl. No. 14/647,626, dated Jul. 28, 2016, 35 pgs.
Office Action in U.S. Appl. No. 14/647,626, dated Jun. 16, 2017, 14 pgs.
Office Action in U.S. Appl. No. 14/647,626, dated Nov. 13, 2017, 18 pgs.
Office Action in U.S. Appl. No. 14/647,649, dated Apr. 19, 2018, 9 pgs.
Office Action in U.S. Appl. No. 14/647,649, dated Dec. 8, 2017, 9 pgs.
Office Action in U.S. Appl. No. 14/647,649, dated May 31, 2017, 11 pgs.
Office Action in U.S. Appl. No. 15/038,078, dated Dec. 21, 2018, 9 pgs.
Office Action in U.S. Appl. No. 15/038,078, dated Mar. 1, 2018, 10 pgs.
Office Action in U.S. Appl. No. 15/038,078, dated Nov. 3, 2017, 10 pgs.
Office Action in U.S. Appl. No. 15/038,078, dated Sep. 11, 2018, 9 pgs.
Office Action in U.S. Appl. No. 15/124,827, dated Dec. 7, 2017, 9 pgs.
Office Action in U.S. Appl. No. 15/322,776, dated Apr. 17, 2018, 27 pgs.
Office Action in U.S. Appl. No. 15/322,776, dated Dec. 10, 2018, 31 pgs.
Office Action in U.S. Appl. No. 15/322,776, dated Jul. 14, 2017, 11 pgs.
Office Action in U.S. Appl. No. 15/322,776, dated Sep. 12, 2017, 23 pgs.
Office Action in U.S. Appl. No. 15/556,370, dated Aug. 2, 2018, 18 pgs.
Office Action in U.S. Appl. No. 15/737,443 dated Feb. 20, 2019, 13 pgs.
Office Action in U.S. Appl. No. 15/737,894, dated Oct. 5, 2018, 27 pgs.
Oh, E.J. et al., "Target specific and long-acting delivery of protein, peptide, and nucleotide therapeutics using hyaluronic acid derivatives," J. Controlled Release vol. 141, 2010, pp. 2-12.
Pal, K. et al., "Biopolymers in Controlled-Release Delivery Systems," Modern Biopolymer Science (2009) 519-557.
Park, Y.D. et al., "Photopolymerized hyaluronic acid-based hydrogels and interpenetrating networks," Biomaterials (2003) 24:893-900.
Pasqui, D. et al., "Polysaccharide-Based Hydrogels: The Key Role of Water in Affecting Mechanical Properties," Polymers (2012) 4:1517-1534.
Patel, P.K et al., "Kinetic studies on the oxidation of phenols by the horseradish peroxidase compound II," Biochim Biophys Acta (1997) 1339(1):79-87.
Perale, G. et al., "Hydrogels in Spinal Cord Injury Repair Strategies," ACS Chem. Neurosci. (2011) 2(7):336-345.
Piggot, A.M. et al., "Synthesis of a new hydrophilic o-nitrobenzyl photocleavable linker suitable for use in chemical proteomics," Tetr. Lett. (2005) 46(47):8241-8244.
Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.
Prestwich, G.D., "Biomaterials from Chemically-Modified Hyaluronan," internet article, Feb. 26, 2001, 17 pgs.
Prestwich, G.D., "Hyaluronic acid-based clinical biomaterials derived for cell and molecule delivery in regenerative medicine," Journal of Controlled Release (2011) 155:193-199.
Price, Richard D. et al., "Hyaluronic acid: the scientific and clinical evidence," J. Plast. Reconstr. Aesthet. Surg. (2007) 60(10)1110-1119.
Qiu, Y. et al., "Environment-sensitive hydrogels for drug delivery," Advanced Drug Delivery Reviews (2001) 53:321-339.
Rao, K.V.R. et al., "Influence of Molecular Size and Water Solubility of the Solute on its Release from Swelling and Erosion Controlled Polymeric Matrices," Journal of Controlled Release (1990) 12:133-141.
Remy, H., Anorganicka chemie II., Sntl Praha 1971, pp. 306-321.
Ritger, P.L. et al., "A Simple Equation for Description of Solute Release I. Fickian and Non-Fickian Release from Non-Swellable Devices in the Form of Slabs, Spheres, Cylinders or Discs," Journal of Controlled Release (1987) 5:23-36.
Akkara, J.A. et al., "Synthesis and Characterization of Polymers Produced by Horseradish Peroxidase in Dioxane," Journal of Polymer Science Part A: Polymer Chemistry (1991) 29(11):1561-1574.
Aldrich, Chem Files Synthetic Methods Oxidation, May 2005, vol. 5, No. 1 pp. 1-11 (English language translation included).
Angelin, M. et al., "Direct, Mild, and Selective Synthesis of Unprotected Dialdo-Glycosides," European Journal of Organic Chemistry (2006):4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem. (1972) 128:1255-1263.
Atkins, E.D.T. et aL, "The Molecular Structure of Hyaluronic Acid," Biochemical Journal (1971) 125(4):92.
Aubry-Rozier, B., Revue Medicale Suisse (2012) 14:571.
Author unknown, "Readily Accessible 12-I-51 Oxidant for the Conversion of Primary and Secondary Alcohols to Aldehydes and Ketones," Journal of Organic Chemistry (1983) 84:4155-4156 (English language on pp. 2-3 of document).

(56) References Cited

OTHER PUBLICATIONS

Author unknown, Encyclopedia of Cellulose, Asakura Publishing Co., Ltd., Nov. 10, 2000, pp. 155-156 (English language translation included).

Baeurle, S.A. et al., "Effect of the counterion behavior on the frictional-compressive properties of chondroitin sulfate solutions," Polymer (2009) 50(7):1805-1813.

Baijal, K P. et al., "Tumor-enhancing effects of cholic acid are exerted on the early stages of colon carcinogenesis via induction of aberrant crypt foci with an enhanced growth phenotype," Canadian Journal of Physiology and Pharmacology, 1998, 76(12), 1095-1102.

Bakke, M. et al., "Identification, characterization, and molecular cloning of a novel hyaluronidase, a member of glycosyl hydrolase family 16, from *Penicillium* spp.," FEBS Letters (2011) 585(1):115-120.

Balan, V. et al., "Strategies to improve chitosan hemocompatibility: A review," European Polymer Journal (2004) 53:171-188.

Banerji, S. et al., "Structures of the Cd44-hyaluronan complex provide insight into a fundamental carbohydrate-protein interaction," Nature structural and molecular biology (2007) 14:234-239.

Benedetti, L. et al., "Biocompatibility and biodegradation of different hyaluronan derivatives (Hyaff) implanted-in rats," Biomaterials (1993) 14(15):1154-1160.

Bezakova, Z. et al., "Effect of microwave irradiation on the molecular and structural properties of hyaluronan," Carbohydrate Polymers (2008) 73(4):640-646.

Bobula, T. et al., "One-pot synthesis of alpha,beta-unsaturated polyaldehyde of chondroitin sulfate," Carbohydrate Polymers (2016) 136:1002-1009.

Bobula, T. et al., "Solid-state photocrosslinking of hyaluronan microfibres," Carbohydrate Polymers (2015) 125:153-160.

Bottegoni, C. et al., "Oral chondroprotection with nutraceuticals made of chondroitin sulphate plus glucosamine sulphate in osteoarthritis," Carb. Pol. (2014) 109:126-138.

Boyer, I.J., "Toxicity of dibutyltin, tributyltin and other organotin compounds to humans and to experimental animals," Toxicology (1989) 55(3), 253-298.

Brand-Williams, W. et al., "Use of a Free Radical Method to Evaluate Antioxidant Activity," LWT—Food Science and Technology (1995) 28:25-30.

Breunig, M. et al., "Breaking up the correlation between efficacy and toxicity for nonviral gene delivery," PNAS (2007) 104(36):14454-14459.

Buffa, R. et al., "Branched hyaluronic acid, synthesis, analysis and biological properties," Journal of Tissue Engineering and Regenerative Medicine (2014) 8(1):321.

Buffa, R. et al., "New method of immobilization of hyaluronic acid oligomers," Journal of Tissue Engineering and Regenerative Medicine (2014) 8(1):321-322.

Burdick, J.A. et al., "Controlled Degradation and Mechanical Behavior of Photopolymerized Hyaluronic Acid Networks," Biomacromolecules (2005) 6:386-391.

Burdick, J.A. et al., "Hyaluronic Acid Hydrogels for Biomedical Applications," Adv. Mater. (2011) 23:H41-H56.

Burke, J., "Solubility Parameters: Theory and Application, The Book and Paper Group Annual, vol. Three, 1984, 62 pgs.

Burner, U. et al., "Transient-state and steady-state kinetics of the oxidation of aliphatic and aromatic thiols by horseradish peroxidase," FEBS Letters (1997) 411(2-3):269-274.

Carey, F.A. et al., Advanced Organic Chemistry Part A: Structure and Mechanisms, Plenum Press, New York and London, pp. 475-479 (1990).

Cayman Chemical, Stearic Acid, obtained online at: https://www.caymanchem.com/pdfs/10011298.pdf, p. 1. (Year: 2017).

Chen, H. et al., "A dual-targeting nanocarrier based on modified chitosan micelles for tumor imaging and therapy," Polym. Chem. 2014, 5, 4734-4746.

Chen, L. et al., "Synthesis and pH sensitivity of carboxymethyl chitosan-based polyampholyte hydrogel for protein carrier matrices," Biomaterials (2004) 25:3725-3732.

Cherrick, G. R. et al., "Indocyanine Green: Observations on Its Physical Properties, Plasma Decay, and Hepatic Extraction," J.Clinical Investigation, 1960, 39, 592-600.

Choi, K. Y. et al., "Self-assembled hyaluronic acid nanoparticles as a potential drug carrier for cancer therapy: synthesis, characterization, and in vivo biodistribution," J. Mater. Chem. 2009, 19 (24), 4102-4107.

Choi, K. Y. et al., "Self-assembled hyaluronic acid nanoparticles for active tumor targeting," Biomaterials 2010, 31 (1), 106-114.

Choi, W. II et al., Targeted antitumor efficacy and imaging via multifunctional nano-carrier conjugated with anti-HER2 trastuzumab, Nanomedicine: Nanotechnology, Biology, and Medicine (2015) 11:359-368.

Chu et al., "Electro-Spinning and Electro-Blowing of Hyaluronic Acid," 2004, Biomacromolecules, vol. 5, pp. 1428-1436. (Year: 2004).

Collins, M. N. et al., "Hyaluronic Acid Based Scaffolds for Tissue Engineering—A review," Carbohydrate Polymers (2013) 92:1262-1279.

Contipro, Specialty Hyaluronan Chemicals Product Catalog, 52 pgs. (retrieved on Sep. 26, 2018). (Year: 2018).

Cornwell, M.J. et al., "A One-Step Synthesis of Cyclodextrin Monoaldehydes," Tetrahedron Letters (1995) 36 (46):8371-8374.

Crescenzi, V. et al., "Novel Hydrogels via Click Chemistry: Synthesis and Potential Biomedical Applications," Biomacromolecules (2007) 8:1844-1850.

Cumpstey, I., Review Article "Chemical Modification of Polysaccharides," ISRN Organic Chemistry (2013) Article ID 417672, 27 pgs.

Czech Official Action in Czech Patent Application No. PV 2008-705, dated Oct. 23, 2009, 2 pgs.

Czech Official Action in Czech Patent Application No. PV 2009-835, dated Aug. 2010, 2 pgs.

Czech Official Action in Czech Patent Application No. PV 2009-836, dated Aug. 6, 2010, 2 pgs.

Czech Search Report in Czech Patent Application No. PV 2010-1001, dated Sep. 27, 2011, 1 pg.

Czech Search Report in Czech Patent Application No. PV 2011-241, dated Nov. 30, 2011, 1 pg.

Czech Search Report in Czech Patent Application No. PV 2012-136, dated Sep. 18, 2012, 3 pgs.

Czech Search Report in Czech Patent Application No. PV 2012-282, dated Jan. 30, 2013, 1 pg.

Czech Search Report in Czech Patent Application No. PV 2012-306, dated Feb. 11, 2013, 1 pg.

Czech Search Report in Czech Patent Application No. PV 2012-664, dated May 24, 2013, 3 pgs.

Czech Search Report in Czech Patent Application No. PV 2012-842, dated Aug. 19, 2013, 3 pgs.

Czech Search Report in Czech Patent Application No. PV 2012-843, dated Aug. 20, 2013, 1 pg.

D'Este, M. et al., "A systematic analysis of *DMTMM* vs *EDC/NHS* for ligation of amines to Hyaluronan in water," Carbohydr. Polym. 2014, 108, 239-246.

Darr, A. et al., "Synthesis and characterization of tyramine-based hyaluronan hydrogels," Journal of Materials Science: Materials in Medicine (2009) 20(1), 33-44.

Dawlee, S. et al., "Oxidized Chondroitin Sulfate-Cross-Linked Gelatin Matrixes: A New Class of Hydrogels," Biomacromolecules (2005) 6(4):2040-2048.

De Figueiredo, R.M. et al., "N,N'-Carbonyldiimidazole-Mediated Cyclization of Amino Alcohols to Substituted Azetidines and Other N-Heterocycles," J. Org. Chem. (2006) 71(11):4147-4154.

Dilling, W.L. et al., "Organic Photochemistry. XII. The Photodimerization and Photoisomerization of 2-Pyridone and Its Monochloro Derivatives," Mol. Photochem. (1973) 5(4):371-409.

Ding, B. et al., "TEMPO-mediated selective oxidation of substituted polysaccharides—an efficient approach for the determination of the degree of substitution at C-6," Carbohydrate Research (2008) 343(18)3112-3116.

Donati, A. et al., "Solution Structure of Hyaluronic Acid Oligomers by Experimental and Theoretical NMR, and Molecular Dynamics Simulation," Biopolymers (2001) 59:434-445.

(56) References Cited

OTHER PUBLICATIONS

Duncan, R. et al., "Nanomedicine(s) under the Microscope," Molecular Pharmaceutics (2011) 8(6):2101-2141.
Dunford, H. B. et al., "Kinetics of the oxidation of p-aminobenzoic acid catalyzed by horseradish peroxidase compounds I and II," J Biol Chem 1975, 250(8), 2920-32.
Eenschooten, C. et al., "Preparation and structural characterisation of novel and versatile amphiphilic octenyl succinic anhydride-modified hyaluronic acid derivatives," Carbohydrate Polymers (2010) 79(3):597-605.
El-Dakdouki, M.H. et al., "Development of drug loaded nanoparticles for tumor targeting. Part 1: synthesis, characterization, and biological evaluation in 2D cell cultures," Nanoscale (2013) 5(9):3895-3903.
El-Dakdouki, M.H. et al., "Development of Multifunctional Hyaluronan-Coated Nanoparticles for Imaging and Drug Delivery to Cancer Cells," Biomacromolecules (2012) 13(4):1144-1151.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 61:385-392.
European First Official Action in European Patent Application No. 10812840.6-1306, dated Jul. 2, 2013, 4 pgs.
European Second Official Action in European Patent Application No. 10812840.6-1306, dated Sep. 24, 2014, 5 pgs.
Feng, Qian et al., "Self-Assembly Behaviour of Hyaluronic Acid on Mica by Atomic Force Microscopy," vol. 20, No. 1, 2004, pp. 146-148 and 152 (English language Abstract p. 152).
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Fleige, E. et al., "Stimuli-responsive polymeric nanocarriers for the controlled transport of active compounds: Concepts and applications," Advanced Drug Delivery Reviews (2012) 64(9):866-884.
Frangioni, J. V., "In vivo near-infrared fluorescence imaging," Curr. Opin. Chem. Biol. (2003) 7(5):626-634.
Funakoshi, T. et al., "Novel chitosan-based hyaluronan hybrid polymer fibers as a scaffold in ligament tissue engineering," Journal of Biomedical Materials Reasearch, Part A (2005) 74A(3):338-346.
Funfstuck, V. V. et al., "Kontaktallergie gegenuber Dicyclohexylcarbodiimid," Dermatosen (1986) 34(4):110-111.
Furuta, T. et al., "Anthraquinon-2-ylmethoxycarbonyl (Aqmoc): A New Photochemically Removable Protecting Group for Alcohols," Org. Lett. (2001) 3(12):1809-1812.
Ghan, R. et al., "Enzyme-Catalyzed Polymerization of Phenols within Polyelectrolyte Microcapsules," Macromolecules (2004) 37(12), 4519-4524.
Gibby, W.A., "Cross-Linked DTPA Polysaccharides for Magnetic Resonance Imaging, Synthesis and Relaxation Properties," Invest. Radio!. 1989, vol. 24, pp. 302-309.
Gilabert, M.A. et al., "Differential substrate behaviour of phenol and aniline derivatives during oxidation by horseradish peroxidase: kinetic evidence for a two-step mechanism," Biochim. Biophys. Acta. (2004) 1699:235-243.
Gilabert, M.A. et al., "Kinetic characterization of phenol and aniline derivates as substrates of peroxidase," Biol. Chem. (2004) 385(9):795-800.
Gilabert, M.A. et al., "Stereospecificity of horseradish peroxidase," Biol. Chem. (2004) 385:1177-1184.
Gobouri, A.A. et al., "Novel Synthesis of Diketo-Acid Chondroitin-4-sulfate as Coordination Biopolymer Precursor trough Oxidation of Chondroitin-4-sulfate by Alkaline Permanganate," International Journal of Sciences (2013) 7:1-11.
Godula, K. et al., "Synthesis of Glycopolymers for Microarray Applications via Ligation of Reducing Sugars to a Poly (acryloyl hydrazide) Scaffold," J. Am. Chem. Soc. (2010) 132:9963-9965.
Gong, J. et al., "Polymeric micelles drug delivery system in oncology," Journal of Controlled Release (2012) 159 (3):312-323.
Green, T.W. et al., "Protective Groups in Organic Synthesis," 1999, New York: John Wiley & Sons, 3rd ed., Chap. 1, pp. 1-16.
Guillaumie, F. et al., "Comparative studies of various hyaluronic acids produced by microbial fermentation for potential topical ophthalmic applications," Journal of Biomedical Materials Research Part A (2009) 1421-1430.
Gupta, P. et al., "Hydrogels: from controlled release to pH-responsive drug delivery," Drug Discovery Today (2002) 7 (10):569-579.
Hacker, M. C. et al., "Multi-Functional Macromers for Hydrogel Design in Biomedical Engineering and Regenerative Medicine," Inter. J. of Mol. Sc. (2015) 16:27677-27706.
Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hassan, R. et al., "Kinetics and mechanism of oxidation of chondroitin-4-sulfate polysaccharide by chromic acid in aqueous perchlorate solutions," (2013) Carbohydrate Polymers 92:2321-6.
Hewson, W. D. et al., "Oxidation of p-cresol by horseradish peroxidase compound I," J Biol Chem 1976, 251 (19), 3036-42.
Hewson, W. D. et al., "Stoichiometry of the reaction between horseradish peroxidase and p-cresol," J Biol Chem 1976, 251(19), 6043-52.
Higashimura, H. et al., Oxidative Polymerization. John Wiley & Sons, Inc. Olefin Fibers (2002) 10:740-764.
Hill, T. K. et al., "Indocyanine Green-Loaded Nanoparticles for Image-Guided Tumor Surgery," Bioconjugate Chem. (2015) 26:294-303.
Hocek, M., "Tvorba C—C A C-X Vazeb Cross-Coupling Reakcemi Katalyzovanymi Komplexy Prechodnych Kovu," Chem. Listy (2003) 97:1145-1150.
Hoffman, A.S., "'Intelligent' Polymers in Medicine and Biotechnology," Artificial Organs (1995) 19(5):458-467.
Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62 (3):611-620.
Horton, D. et al., "Synthesis of 2,3-Unsaturated Polysaccharides From Amylose and Xylan," Carbohydrate Research (1975) 40:345-352.
Ritger, P.L. et al., "A Simple Equation for Description of Solute Release II. Fickian and Anomalous Release from Swellable Devices," Journal of Controlled Release (1987) 5:37-42.
Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.
Rowe et al., "Handbook of Pharmaceutical Excipients," 6th edition, 2009, Pharmaceutical Press, pp. 110-114 and 581-585. (Year: 2009).
Ruoslahti, E. et al., "Targeting of drugs and nanoparticles to tumors," The Journal of Cell Biology (2010) 188 (6):759-768.
Rupprecht, A., "Wet Spinning of Hyaluronic Acid. Preparation of Oriented Samples; Acta Chemica Scandinavica; 1979; 33; 779-780.
Saettone et al., "Evaluation of muco-adhesive properties and in vivo activity of ophthalmic vehicles based on hyaluronic acid," 1989, International Journal of Pharmaceutics, vol. 51, pp. 203-212 (Year: 1989).
Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.
Schachter, D., "The Source of Toxicity in CTAB and CTAB-Stabilized Gold Nanorods," MS thesis submitted to Graduate School-New Brunswick Rutgers, The State University of New Jersey and the Graduate School of Biomedical Sciences, University of Medicine and Dentistry of New Jersey, 2013, 70 pgs.

(56) References Cited

OTHER PUBLICATIONS

Schante, C.E. et al., "Chemical modifications of hyaluronic acid for the synthesis of derivatives for a broad range of biomedical applications," Carbohydrate Polymers (2011) 85:469-489.
Scott, J.E. et al., "Periodate Oxidation of Acid Polysaccharides", Histochemie, Apr. 26, 1969, vol. 19, pp. 155-161.
Scott, J.E. et al., "Secondary and tertiary structures of hyaluronan in aqueous solution, investigated by rotary shadowing—electron microscopy and computer simulation," J. Biochem vol. 274, 1991, pp. 699-705.
Sedova, P. et al., "Preparation of hyaluronan polyaldehyde—a precursor of biopolymer conjugates," Carbohydrate Research (2013) 371:8-15.
Seidlits, S.K. et al., "The effects of hyaluronic acid hydrogels with tunable mechanical properties on neural progenitor cell differentiation" Biomaterials (2010) 31:3930-3940.
Shang, J. et al., "Chitosan-based electroactive hydrogel," Polymer (2008) 49:5520-5525.
Sheehan, J.K. et al., "X-ray Diffraction Studies on the Connective Tissue Polysaccharides," J. Mol. Biol. (1975) X1:153-163.
Shen, Yan et al., "Synthesis and characterization of low molecular weight hyaluronic acid-based cationic micelles for efficient siRNA delivery," Carbohydrate Polymers (2009) 77(1):95-104.
Shen, Yi et al., "Synthesis, Characterization, Antibacterial and Antifungal Evaluation of Novel Monosaccharide Esters," Molecules (2012) 17(7):8661-8673.
Shimizu, M. et al., "Studies on hyaluronidase, chondroitin sulphatase, proteinase and phospholipase secreted by *Candida* species," MYCOSES (1996) 39:161-167.
Shutava, T. et al., "Microcapsule Modification with Peroxidase-Catalyzed Phenol Polymerization," Biomacromolecules (2004) 5(3):914-921.
Sieburth, S.M. et al., "Fusicoccin Ring System by [4 + 4] Cycloaddition. 2. A Model Study," Tetrahedron Letters (1999) 40:4007-4010.
Sieburth, S.M. et al., "The [4 + 4] Cycloaddition and its Strategic Application in Natural Product Synthesis," Tetrahedron (1996) 52(18):6251-6282.
Slaughter, B.V. et al., "Hydrogels in Regenerative Medicine," Advanced Materials (2009) 21(32-33):3307-3329.
Slezingrova, K. et al., "Synteza a charakterizace palmitoyl hyaluronanu," Chemicke Listy (2012) 106:554-567.
Smeds, K.A. et al., "Photocrosslinkable polysaccharides for in situ hydrogel formation," J. Biomed. Mater. Res. (2001) 54:115-121.
Smejkalova, D. et al., "Structural and conformational differences of acylated hyaluronan modified in protic and aprotic solvent system," Carbohydrate Polymers (2012) 87(2):1460-1466.
Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.
Su, W.Y. et al., "Injectable oxidized hyaluronic acid/adipic acid dihydrazide hydrogel for nucleus pulposus regeneration," Acta. Biomater. (2010) 6(8):3044-3055.
Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.
Tan, H. et al., "Injectable in situ forming biodegradable chitosan-hyaluronic acid based hydrogels for cartilage tissue angineering," Biomaterials (2009) 30(13):2499-2506.
Tan, X. X et al., "A NIR heptamethine dye with intrinsic cancer targeting, imaging and photosensitizing propeties," Biomaterials (2012) 33:2230-2239.
Tankam, P.F. et al., "Alkynyl polysaccharides: synthesis of propargyl potato starch followed by subsequent derivatizations," Carbohydrate Research (2007) 342:2049-2060.
Tao, Y. et al., "Core cross-linked hyaluronan-styrylpyridinium micelles as a novel carrier for paclitaxel," Carbohydrate Polymers (2012) 88(1):118-124.

Testa, G. et al., "Influence of dialkyne structure on the properties of new click-gels based on hyaluronic acid," International Journal of Pharmaceutics (2009) 378:86-92.
Thakar, D. et al., "A quartz crystal microbalance method to study the terminal functionalization of glycosaminoglycans," Chemical Communications (2014) 50(96):15148-15151.
Thelin, M. et al., "Biological functions of iduronic acid in chondroitin/dermatan sulfate," FEBS Journal (2013) 280:2431-2446.
Thomas, R. G. et al, "Hyaluronic acid conjugated superparamagnetic iron oxide nanoparticle for cancer diagnosis and hyperthermia therapy," Carbohydrate Polymers 131 (2015) pp. 439-446.
Til, H.P. et al., "Acute and Subacute Toxicity of Tyramine, Spennidine, Spennine, Putrescine and Cadaverine in Rats," Food and Chemical Toxicology (1997) 35(3-4):337-348.
Tonelli, A.E., "Effects of crosslink density and length on the number of intramolecular crosslinks (defects) introduced into a rubbery network," Polymer (1974) 15(4):194-196.
Tornoe, C. et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem. (2002) 67:3057-3064.
Um, I.C. et al., "Electro-Spinning and Electro-Blowing of Hyaluronic Acid," Biomacromolecules (2004) 5:1428-1436.
Uyama, H. et al., "Enzymatic Synthesis of Polyphenols," Current Organic Chemistry (2003) 7:1387-1397.
Van Bommel, K.J.C. et al., "Responsive Cyclohexane-Based Low-Molecular-Weight Hydrogelators with Modular Architecture," Angew. Chem. Int. Ed. (2004) 1663-1667.
Veitch, N.C., "Horseradish peroxidase: a modern view of a classic enzyme," Phytochemistry (2004) 65:249-259.
Vigo, T. L et al., "Deoxycelluloses and Related Structures," Polymers for Advanced Technologies (1999) 10:311-320.
Wang, J. et al., "Polymeric Micelles for Delivery of Poorly Soluble Drugs: Preparation and Anticancer Activity in Vitro of Paclitaxel Incorporated into Mixed Micelles Based on Poly(ethylene Glycol)-Lipid Conjugate and Positively Charged Lipids," Journal of Drug Targeting (2005) 13(1):73-80.
Wang, W. et al., "Developing Fluorescent Hyaluronan Analogs for Hyaluronan Studies," Molecules 2012, 17, 1520-1534.
Wang, X. et al., "Formation of water-resistant hyaluronic acid nanofibers by blowing-assisted electro-spinning and nontoxic post treatments," Polymer (2005) 46:4853-4867.
Weng, L. et al., "In vitro and in vivo suppression of cellular activity by guanidinoethyl disulfied released from hydrogel microspheres composed of partially oxidized hyaluronan and gelatin," Biomaterials, Aug. 3, 2008, vol. 29, pp. 4149-4156.
Weng, L. et al., "Self-crosslinkable hydrogels composed of partially oxidized hyaluronan and gelatin: in vitro and in vivo responses," Journal of Biomedical Materials Research Part A, Aug. 9, 2007, pp. 352-365.
Wermuth, C.G., "Similarity in drugs: reflections on analogue design," Drug Discovery Today (2006) 11(718):348-354.
Huang, G. et al., "Superparamagnetic Iron Oxide Nanoparticles: Amplifying ROS Stress to Improve Anticancer Drug Efficacy.," Theranostics (2013) 3(2):116-126.
Huang, L. et al., "A Facsimile Method for Oxidation of Primary Alcohols to Caroxylic Acids and Its Application in Glycosaminoglycan Syntheses," Chemistry (2006) 12(20):5246-5252.
Huerta-Angeles, G. et al., "Novel synthetic method for the preparation of amphiphilic hyaluronan by means of aliphatic aromatic anhydrides," Carbohydrate Polymers (2014) 111:883-891.
Huerta-Angeles, G. et al., "Synthesis of highly substituted amide hyaluronan derivatives with tailored degree of substitution and their crosslinking via click chemistry," Carbohydrate Polymers (2011) 84:1293-1300.
Huh, K.M. et al., "Hydrotropic polymer micelle system for delivery of paclitaxel," Journal of Controlled Release (2005) 101:59-68.
Hussain, M. A. et al., "Acylation of Cellulose with N,N'-Carbonyldiimidazole-Activated Acids in the Novel Solvent Dimethyl Sulfoxide/Tetrabutylammonium Fluoride," Macromol. Rapid Commun. (2004) 25:916-920.
Hynes, W.L. et al., "Hyaluronidases of Gram-positive bacteria," FEMS Microbiology Letters (2000) 183:201-207.

(56) References Cited

OTHER PUBLICATIONS

Inanaga, J. et al., "A Rapid Esterification by Means of Mixed Anhydride and Its Application to Large-ring Lactonization," Bulletin of the Chemical Society of Japan (1979) 52(7):1989-1993.
International Preliminary Report on Patentability in International Patent Application No. PCT/CZ2010/000128, dated Feb. 5, 2013, 5 pgs.
International Preliminary Report on Patentability in International Patent Application No. PCT/CZ2010/000129, dated Jun. 12, 2012, 5 pgs.
International Search Report in International Patent Application No. PCT/CZ2009/000131, dated Apr. 9, 2010, 3 pgs.
International Search Report in International Patent Application No. PCT/CZ2010/000030, dated Sep. 1, 2010, 3 pgs.
International Search Report in International Patent Application No. PCT/CZ20101000128, dated Jun. 9, 2011, 3 pgs.
International Search Report in International Patent Application No. PCT/CZ2010/000129, dated Jun. 15, 2011, 3 pgs.
International Search Report in International Patent Application No. PCT/CZ2011/000126, dated Apr. 12, 2012, 3 pgs.
International Search Report in International Patent Application No. PCT/CZ2012/000035, dated Aug. 28, 2012, 3 pgs.
International Search Report in International Patent Application No. PCT/CZ2013/000023, dated Aug. 9, 2013, 3 pgs.
International Search Report in International Patent Application No. PCT/CZ2013/000057, dated Jul. 24, 2013, 4 pgs.
International Search Report in International Patent Application No. PCT/CZ2013/000063, dated Apr. 23, 2015, 7 pgs.
International Search Report in International Patent Application No. PCT/CZ2013/000091, dated Oct. 31, 2013, 3 pgs.
International Search Report in International Patent Application No. PCT/CZ2013/000116, dated Jan. 28, 2014, 4 pgs.
International Search Report in International Patent Application No. PCT/CZ2013/000155, dated Feb. 19, 2014, 4 pgs.
International Search Report in International Patent Application No. PCT/CZ2013/000156, dated Apr. 4, 2014, 5 pgs.
International Search Report in International Patent Application No. PCT/CZ2013/000157, dated Mar. 19, 2014, 3 pgs.
International Search Report in International Patent Application No. PCT/CZ2013/000158, dated Mar. 19, 2014, 3 pgs.
International Search Report in International Patent Application No. PCT/CZ2014/000138, dated May 4, 2015, 4 pgs.
International Search Report in International Patent Application No. PCT/CZ2015/000018, dated Jul. 22, 2015, 5 pgs.
International Search Report in International Patent Application No. PCT/CZ2015/000068, dated Jan. 8, 2016, 4 pgs.
International Search Report in International Patent Application No. PCT/CZ2016/000027, dated Jun. 27, 2016, 3 pgs.
International Search Report in International Patent Application No. PCT/CZ2016/000065, dated Sep. 30, 2016, 5 pgs.
International Search Report in International Patent Application No. PCT/CZ2016/000071, dated Oct. 10, 2016, 4 pgs.
International Search Report in International Patent Application No. PCT/CZ2016/050036, dated Feb. 6, 2017, 4 pgs.
International Search Report in International Patent Application No. PCT/CZ2016/050048, dated May 3, 2017, 4 pgs.
International Search Report in International Patent Application No. PCT/CZ2017/050026, dated Oct. 26, 2017, 2 pgs.
International Search Report in International Patent Application No. PCT/EP2016/064653, dated Aug. 25, 2016, 4 pgs.
Jacoboni, I., "Hyaluronic Acid by Atomic Force Microscopy," Journal of Structural Biology vol. 126, 1999, pp. 52-58.
Jahn, M. et al., "The reaction of hyaluronic acid and its monomers glucuronic acid and N-acetylglucosamine, with reactive oxygen species," Carbohydrate Research, 1999, vol. 321, pp. 228-234.
Japanese Official Action (English language translation) in Japanese Patent Application No. 2012-542355, dated Oct. 17, 2014.
Japanese Official Action (English language translation) in Japanese Patent Application No. 2014-506754, dated Jan. 22, 2015, 2 pgs.
Japanese Official Action (including English language translation) in Japanese Patent Application No. 2012-542356, dated Oct. 3, 2014, 8 pgs.
Japanese Official Action in Japanese Patent Application No. 2015-543316, 5 pgs.
Ji, Y. et al., "Electrospun three-dimensional hyaluronic acid nanofibrous scaffolds," Biomaterials (2006) 27 (1):3782-3792.
Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.
Jiang, B. et al., "Study on TEMPO-mediated selective oxidation of hyaluronan and the effects of salt on the reaction kinetics," Carbohydrate Research, Pergamon, GB (2000) 327(4)455-461.
Jin, R. et al., "Enzyme-mediated fast in situ formation of hydrogels from dextran-tyramine conjugates," Biomaterials (2007) 28(18):2791-2800.
Job, D. et al., "Substituent effect on the oxidation of phenols and aromatic amines by horseradish peroxidase compound I," Eur J Biochem 1976, 66 (3), 607-14.
Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.
Juhlin, L., "Hyaluronan in skin," Journal of Internal Medicine (1997) 242:61-66.
Kalyanaraman, B. et al., "Peroxidatic oxidation of catecholamines. A kinetic electron spin resonance investigation using the spin stabilization approach" Journal of Biological Chemistry (1984) 259(12)7584-7589.
Katritzky, A.R. et al., "Cycloaddition Reactions of Heteroaromatic Six-Membered Rings," Chem. Rev. (1989) 39:827-861.
Katz, S.A. et al., "The Toxicology of Chromium with Respect to its Chemical Speciation: a Review," Journal of Applied Toxicology (1993) 13(3):217-224.
Kawaguchi, Y. et al., "The relation between the adsorption behavior at the interface and the conformational changes in hyaluronates partially modified with various acyl chains," Carbohydrate Polymers (1995) 26:149-154.
Kedar, U. et al., "Advances in polymeric micelles for drug delivery and tumor targeting," Nanomedicine: Nanotechnology, Biology, and Medicine (2010) 6(6):714-729.
Kelly, S. J. et al., "Kinetic properties of *Streptococcus pneumoniae* hyaluronate lyase," Glycobiology (2001) 11 (4):297-304.
Khademhosseini, A. et al., "Layer-by-layer deposition of hyaluronic acid and poly-L-lysine for patterned cell co-cultures," Biomaterials (2004) 25:3583-3592.
Khetan, S. et al., "Patterning network structure to spatially control cellular remodeling and stem cell fate within 3-dimensional hydrogels," Biomaterials (2010) 31(32):8228-8234.
Khetan, S. et al. "Sequential crosslinking to control cellular spreading in 3-dimensional hydrogels," Soft Matter (2009) 5:1601-1606.
Kim, B. et al., "Complexation Phenomena in pH-Responsive Copolymer Networks with Pendent Saccarides," Macromol. (2002) 35:9545-9550.
Kim, T.G. et al., "Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel," Biomacromolecules (2009) 10(6):1532-1539.
Klan, P. et al., "Photoremovable Protecting Groups in Chemistry and Biology: Reaction Mechanisms and Efficacy," Chem. Rev. (2013) 113(1):119-191.
Kobayashi, H. et al., "New Strategies for Fluorescent Probe Design in Medical Diagnostic Imaging," Chem. Rev. (2010) 110(5):2620-2640.
Kokuryo, D. et al., "Corrigendum to SPIO-PICsome: Development of a highly sensitive and stealth-capable MRI nano-agent for tumor detection using SPIO-loaded unimellar polyion complex vesicles (PICsomes)," Journal of Controlled Release (2014) 178:125.
Korsmeyer, R.W. et al., "Mechanisms of solute release from porous hydrophilic polymers," International Journal of Pharmaceutics (1983) 15:25-35.

(56) References Cited

OTHER PUBLICATIONS

Kumar, A. et al., "Development of hyaluronic acid-Fe2O3 hybrid magnetic nanoparticles for targeted delivery of peptides," Nanomedicine: Nanotechnology, Biology and Medicine, Elsevier, NL (2007) 3(2)132-137.
Kuo, J.W., "Practical Aspects of Hyaluronan Based Medical Products," 2006, CRC Press, Taylor & Francis Group, pp. 60-61.
Kühn, A. V. et al., "Identification of hyaluronic acid oligosaccharides by direct coupling of capillary electrophoresis with electrospray ion trap mass spectrometry," Rapid Communications in Mass Spectrometry (2003) 17:576-582.
Lapcik, L. Jr. et al., Chemicke Listy vol. 85, 1991, pp. 281-298.
Laurent, S. et al., "Magnetic fluid hyperthennia: Focus on superparamagnetic iron oxide nanoparticles," Advances in Colloid and Interface Science (2011) 166:8-23.
Leach, J.B. et al., "Characterization of protein release from photocrosslinkable hyaluronic acid-polyethylene glycol hydrogel tissue engineering scaffolds," Biomaterials (2005) 26:125-135.
Leach, J.B. et al., "Photocrosslinked Hyaluronic Acid Hydrogels: Natural, Biodegradable Tissue Engineering Scaffolds," Biotechnol Bioeng. (2003) 82:578-589.
Lee, Dong-Eun et al., "Amphiphilic hyaluronic acid-based nanoparticles for tumor-specific optical/MR dual imaging," Journal of Materials Chemistry (2012) 22(1):10444-10447.
Lee, Dong-Eun et al., "Hyaluronidase-Sensitive SPIONs for MR/Optical Dual Imaging Nanoprobes," Marcomol. Res. (2011) 19(8):861-867.
Lee, F. et al., "An injectable enzymatically crosslinked hyaluronic acid-tyramine hydrogel system with independent tuning of mechanical strength and gelation rate," Soft Matter (2008) 4:880-887.
Lee, F. et al., "An injectable hyaluronic acid-tyramine hydrogel system for protein delivery," Journal of Controlled Release (2009) 134:186-193.
Lee, K.Y. et al., "Electrospinning of polysaccharides for regenerative medicine," Advanced Drug Delivery Reviews (2009) 61:1020-1032.
Lee, S.A. et al., "Spectroscopic studies of the physical properties of hyaluronate films: the origin of the phase transition," Carbohydrate Polymers (1995) 28:61-67.
Lee, Yuhan et al., "Bioinspired Surface Immobilization of Hyaluronic Acid on Monodisperse Magnetite Nanocrystals for Targeted Cancer Imaging," Advanced Materials (2008) 20:4154-4157.
Li, J. et al., "Electrospinning of Hyaluronic Acid (HA) and HA/Gelatin Blends," Macromolecular Rapid Communications (2006) 27:114-120.
Li, J. et al., "Redox-sensitive micelles self-assembled from amphiphilic hyaluronic acid-deoxycholic acid conjugates for targeted intracellular delivery of paclitaxel," Biomaterials (2012) 33(7):2310-2320.
Li, M. et al., Comparison of Two Ultrasmall Superparamagnetic Iron Oxides on Cytotoxicity and MR Imaging of Tumors, Theranostics (2012) 2(1):76-85.
Liang, Y. et al., "An in situ formed biodegradable hydrogel for reconstruction of the corneal endothelium," Colloids and Surfaces B: Biointerfaces (2011) 82(1):1-7.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008 (English language Abstract on p. 3).
Liu, Yanchun et al., "Biocompatibility and stability of disulfide-crosslinked hyaluronan films," Biomaterials (2005) 26 (23):4737-4746.
Liu, Yanhua et al., "Dual targeting folate-conjugated hyaluronic acid polymeric micelles for paclitaxel delivery," International Journal of Pharmaceutics (2011) 421(1):160-169.
Luo, S. et al., "A review of NIR dyes in cancer targeting and imaging," Biomaterials (2011) 32:7127-7138.
Luo, Yanfeng et al., "Novel amphoteric pH-sensitive hydrogels derived from ethylenediaminetetraacetic dianhydride, Dutanediamine and amino-terminated poly(ethylene glycol): Design, synthesis and swelling behavior," European Polymer Journal (2011) 47:40-47.
Maeda, H., "The Enhanced Permeability and Retention (EPR) Effect in Tumor Vasculature: The Key Role of Tumor-Selective Macromolecular Drug Targeting," Advances in Enzyme Regulation (2001) 41(1):189-207.
Malkoch, M. et al., "Synthesis of well-defined hydrogel networks using Click chemistry," Chem. Commun. (2006) 2774-2776.
Marega, R. et al., "Hyaluronan-Carbon Nanotube Derivatives: Synthesis, Conjugation with Model Drugs, and DOSY NMR Characterization," Eur J. Org. Chem. (2011) 28:5617-5625.
Matsushima, R. et al., "Photoreactions of Alkylated 2-Pyridones," J. Chem. Soc. Perkin Trans. 2 (1985) 1445-1448.
Mayol, L. et al., "Amphiphilic hyaluronic acid derivatives toward the design of micelles for the sustained delivery of hydrophobic drugs," Carbohydrate Polymers (2014) 102:110-116.
Mazzone, S.B., "Fluorescent styryl dyes FM 1-43 and FM2-10 are muscarinic receptor antagonists: intravital visualization of receptor occupancy," The Journal of Physiology (2006) 575(1):23-35.
McIntyre, J.E., "The Chemistry of Fibres," Studies in Chemistry No. 6, 1971, p. 15.
McTaggart, L.E. et al., "Assessment of polysaccharide gels as drug delivery vehicles," Int. J. Pharm. 1993, vol. 100, pp. 199-206.
Mero, A. et al., "Hyaluronic Acid Bioconjugates for the Delivery of Bioactive Molecules," Polymers (2014) 6(2):346-369.
Merriam Webster Online Dictionary, obtained online at: http://www.merriam-webster.com/cgi-bin/dictionary?book=Dictionary&va=derivative, downloaded on Jul. 5, 2008.
Miki, K. et al., "Near-Infrared Dye-Conjugated Amphiphilic Hyaluronic Acid Derivatives as a Dual Contrast Agent for in Vivo Optical and Photoacoustic Tumor Imaging," Biomacromolecules (2015) 16:219-227.
Milas, M. et al., "Characterization and Properties of Hyaluronic Acid (Hyaluronan)," Polysaccharides: Structural Diversity and Functional Versatility, by S. Dumitriu 1998, Marcel Dekker Inc., pp. 535-549.
Miller, R.J. et al., Chemistry and Biology of Hyaluronan : Medicinal Uses of Modified Hyaluronate. Elsevier Ltd. 2004. 505-528.

UNSATURATED DERIVATIVES OF POLYSACCHARIDES, METHOD OF PREPARATION THEREOF AND USE THEREOF

FIELD OF THE INVENTION

The invention relates to polysaccharide derivatives comprising, in their structure, a heterocycle having a double bond in positions 4 and 5 according to the structural formula X, where R represents —NH—CO—CH$_3$ or —OH.

Further, the invention relates to the preparation of the derivatives of the formula X from a starting polysaccharide comprising the structural fragment Y, where the modification itself can be simplified into the following scheme:

where R represents —NH—CO—CH$_3$ or —OH, and R$^1$ represents —SO$_2$—ONa, —SO$_2$—OH, or —H, whereas the absolute configuration on carbon 4 can be R or S.

Further the invention relates to the use of these unsaturated derivatives that, in contrast to native polysaccharides, show enhanced antioxidant properties, and some of them selectively inhibit cancer cells proliferation.

BACKGROUND OF THE INVENTION

Polysaccharides of General formula Y

Polysaccharides have a wide range of functions in organisms, such as building, stocking, or regulatory function. The polysaccharides of the general formula Y also belong to the polymers naturally occurring in organisms.

where R represents CH$_3$—CO—NH— or —OH, and R$^1$ represents —SO$_2$—ONa, —SO$_2$—OH, or —H. This comprises for example chondroitin sulfate, dermatan sulfate, carrageenan, keratan sulfate, or hyaluronic acid.

Chondroitin sulfate is linear, sulfated, and negatively charged glycosaminoglycan composed of repeating monomer units of N-acetyl-D-galactosamine and D-glucuronic acid, linked with each other by β(1→3) and β(1→4) O-glycosidic bonds (the structural formula of chondroitin sulphate see below), where
R$^1$ is —H or —Na,
R$^2$ is —H, —SO$_2$—ONa or —SO$_2$—OH.

Chondroitin sulfate is derived from animal connective tissues where it is bound on proteins and thus forms part of proteoglycans. The sulfation of chondroitin is realized by means of sulfotransferases in various positions and by various types. The unique pattern of sulfation in particular positions in the polymer chain encodes the specific biologic activity of chondroitin sulfate. Chondroitin sulphate is an important structural block of cartilage in joints, providing them with compressive strength and renewing the balance of joint lubrication fluid composition (Baeurle S. A. a kol. *Polymer* 50, 1805, 2009).

Dermatan sulfate is linear, sulfated, and negatively charged glycosaminoglycan composed of repeating monomer units of N-acetyl-D-galactosamine and L-iduronic acid, linked with each other by β(1→3) and β(1→4) O-glycosidic bonds (the structural formula of dermatan sulfate see below), where
R$^1$ is —H or —Na,
R$^2$ is —H, —SO$_2$—OH or —SO$_2$—ONa.

Dermatan sulfate differs from chondroitin sulfate by the presence of L-iduronic acid that is C-5 epimere of D-glukuronic acid. The inverse configuration of iduronic acid confers better flexibility to dermatan sulfate chains and ensures their specific glycosaminoglycan-protein interaction in the surrounding area. These interactions contribute to the regulation of several cell processes, such as migration, proliferation, differentiation, or angiogenesis. The conversion of chondroitin sulfate into dermatan sulfate is ensured by means of three enzymes, namely dermatan sulfate epimerase 1 (DS-epi1), dermatan sulfate epimerase 2 (DS-epi2), and dermatan 4-O-sulfotransferase (D4ST1) (Thelin M., et al. *FEBS Journal* 280, 2431, 2013).

Keratan sulfate belongs to the group of linear sulfated polysaccharides comprising D-galactose, N-acetylglucosamine, and galactose-6-sulfate linked with β(1→3) and β(1→4) bonds, having the structure and bonds similar to chondroitin sulfate. It can be found in cornea, cartilages, bones, and connective tissue (the structural formula of keratan sulfate see below), where $R^2$ is —H, —$SO_2$—OH, or —$SO_2$—ONa.

Carrageenans belong to the group of linear sulfated polysaccharides that are obtained by the extraction of red sea algae. Galactose and its 3,6-anhydro derivative are their basic structural units, linked to each other by β(1→3) and β(1→4) O-glycosidic bonds. There exist three main groups of carrageenans that differ in the degree of sulfation and water solubility. Kappa-carrageenan has one sulfate group in dimer and forms stiff gels in aqueous environment. Iota-carrageenan contains two sulfates and forms soft gels, whereas lambda-carrageenan having three sulfates does not exhibit any gelling properties.

Hylauronic acid is non-sulfated glycosaminoglycan composed of two repeating units of D-glucuronic acid and N-acetyl-D-glucosamine.

where
$R^1$ is H or Na.

The molecular weight of native hyaluronic acid is in the range of $5.10^4$ to $5.10^6$ g·mol$^{-1}$. This very hydrophilic polysaccharide is a part of connective tissues, skin, joint synovial fluid; it plays an important role in many biological processes, such as proteoglycanes organisation, cells hydration and differentiation. As this polymer occurs naturally in the body and thus it is biodegradable, it is useful as a substrate in the field of tissue engineering or as a carrier of biologically active substances.

Polysaccharides Containing Multiple Bonds

Polysaccharides having —C═C— multiple bond that forms a part of saccharide cycle and is not situated at the end of the chain are very rare. As an example of common polysaccharides, 5,6-unsaturated derivatives of cellulose, known as cellulosenes (Vigo T. L. et al. *Polymers for Advanced Technologies*, 10, 6, 311-320, 1999) or their 2,3-unsaturated analogues are described. The method of the preparation of 5,6-unsaturated derivatives is based on elimination reaction of the leaving group in the position 6 and hydrogen in the position 5 under basic conditions to produce enol ether (—C═C— multiple bond is conjugated with heterocyclic oxygen). The preparation of 2,3-unsaturated derivatives of cellulose, amylose, or xylan (D. Horton et al. *Carbohydrate Research*, 40, 2, 345-352, 1975) requires, in addition to the presence of leaving groups, a reducing agent, usually zinc, to produce a standard alkene (without the conjugation of multiple bond and oxygen).

Utilization of polysaccharides Containing Multiple Bonds

The applications are aimed mostly at the modification of —C═C— multiple bond that is not a direct part of the saccharide cycle. These methods are based on bonding a new substance to the polymer skeleton, where the structure is changed in an important way, i.e. the native character of the polysaccharide is lost. In such cases, the multiple bond is normally used in polymerization (Bellini D. WO96/37519), addition (Khetan S. et al. *Soft Matter*, 5, 1601-1606, 2009) or cycloaddition reactions (Nimmo Ch. M. et al. *Biomacromolecules*, 12, 824-830, 2011; Bobula, T. et al. *Carbohydrate. Polymers*, 125, 153-160, 2015). These methods can lead to both effective crosslinking of polysaccharides (Collins M. N. et al. *Carbohydrate Polymers*, 92, 1262-1279, 2013; Hacker M. C. et al., *Inter. J, of Mol. Sc.*, 16, 27677-706, 2015), and selective bonding of active substances to the polymer (Mero A. et al. *Polymers*, 6, 346-369, 2014). The multiple bond of methacrylate group is also very commonly used to perform a polymerization reaction (Granstrom M. a kol. EP2899214).

There are only a few methods of introducing the multiple —C═C— bond directly into the saccharide cycle in a polymer chain. One of them is an enzymatic cleavage of polymers by lyases, where the double bond is formed at the non-reducing end of the polymer (Kelly S. J. a kol. *Glycobiology*, 11, 4, 294-304, 2001), which is, in this case, hyaluronic acid (see the scheme below).

It means that the occurrence of this modification strongly depends on the molecular weight; for example, for the molecular weight of $4.10^4$ g·mol$^{-1}$ only one of one hundred disaccharides is modified, if the molecular weight is $4.10^5$ g·mol$^{-1}$, one of one thousand disaccharides is modified. Thus, it is obvious that, except for polysaccharide oligomers, this type of modification is minor and there is actually no difference between the starting and the resulting high molecular polymer.

The second method enables incorporating the double bond into the polysaccharide structure in the positions 4 and 5 along the whole chain length, so the polymers having a higher molecular weight can be efficiently modified (Buffa R. et al. WO2014/023272, Bobula T. et al. *Carbohydrate Polymers*, 136, 1002-1009, 2016). However, in this method, multiple —C═C— bond is formed, and this bond is directly conjugated with strong electron acceptor aldehyde group. This modification significantly changes chemical properties of the polysaccharide, because it enables covalent bonding of wide range of nucleophiles, usually amines. The above mentioned fact also implies that the polymer modified in this way has significantly higher electrophile characteristic and thus it chemically differs from the native polymer. It can be also considered as less active antioxidant comparing to the non-modified polymer.

The solution described in this invention can eliminate these drawbacks; there is no reactive electrophile group in the modified polymer, compared to the non-modified polymer. On the contrary, the double bond conjugated with heterocyclic oxygen can be considered as a group having nucleophilic (antioxidant) properties.

SUMMARY OF THE INVENTION

Subject of the invention is polysaccharide derivatives comprising, in their structure, the heterocycle having the double bond in positions 4 and 5 according to the structural formula X,

X where R is —NH—CO—CH$_3$ or —OH.

The molecular weight of the derivatives is in the range of $5.10^3$ to $5.10^5$ g·mol$^{-1}$, and the starting polysaccharides for the preparation of the derivatives according to the invention are preferably selected from the group comprising chondroitin sulfate, carrageenan, dermatan sulfate, hyaluronic acid or keratan sulfate.

Further, the invention relates to the method of preparation, based on three steps (see the scheme below):

where R is —NH—CO—CH$_3$ or —OH, and R$^1$ is —SO$_2$—ONa, —SO$_2$—OH or —H

1. Oxidation—introducing an aldehyde group in the position 6 of the saccharide cycle. Oxidation of the primary hydroxyl group in the position 6 to an aldehyde. The reaction can be performed for example by means of 2,2,6,6-tetramethyl-1-piperidinyloxyl radical TEMPO/NaClO oxidation system in water. This step is preferably conducted in water at the temperature of 0 to 10° C., with NaClO in molar amount of 0.03 to 0.8 eq. and molar amount of TEMPO in the range of 0.005 to 0.2 eq. with respect to the repeating unit of the polysaccharide. The starting polysaccharide can have the molecular weight in the range of $5.10^3$ to $5.10^5$ g·mol$^{-1}$ and 0.1 to 8% wt. aqueous solution of polysaccharide is preferably used. Finally, ethanol, sodium thiosulfate etc. can be added to the reaction mixture to end the reaction and eliminate the residuals of the unreacted agent (hypochlorite). Alternatively, the oxidation can be performed by means of 1,1,1-triacetoxy-1,1-dihydro-1,2-benziodoxol-3 (1H)-one (DMP) system at the temperature of 10° C. to 50° C. in DMSO, where the amount of DMP is in the range of 0.05 to 2 eq. with respect to the repeating unit of the polysaccharide.

2. Elimination

2a. if R$^1$=—H, elimination of water is performed (dehydration).

It can be preferably conducted in aqueous-organic media, where the organic solvent is water-miscible and the volume ratio of solvent/water is in the range of 3/1 to 1/2. Preferably, the base such as pyridine, triethylamine, or N,N-diisopropylethylamine, or an inorganic base, e.g. Ca(OH)$_2$, can be used in this step. The amount of the base in the reaction is 0.01 to 20 eq., preferably 5 to 10 eq., based on the repeating unit of the polysaccharide. As organic solvents, water miscible aprotic polar solvents can be used, preferably DMSO or sulfolane. The oxidation is performed for 0.1 to 12 hours, preferably 1 to 4 hours; the second step of the reaction is performed for 12 to 150 hours, preferably 20 to 40 hours, at the temperature of 30 to 80° C., preferably 50 to 60° C.

2b. if R$^1$=—SO$_2$—ONa or SO$_2$—OH, elimination of NaO—SO$_2$—ONa or HO—SO$_2$—ONa respectively, is performed. If —OR$^1$ group in the position 4 in the cycle is in the antiperiplanar position with respect to hydrogen in the position 5, elimination proceeds spontaneously without the need of addition of bases and without the need of increasing the reaction temperature. Duration of the reaction of the steps 1+2b is 0.1 to 12 hrs, preferably 1 to 4 hrs. If —OR$^1$ group in the position 4 of saccharide cycle is not in the antiperiplanar position with respect to hydrogen in the position 5, the method described in the part 2a can be also used for an effective elimination.

3. Reduction—aldehyde group is selectively reduced with borohydrides, preferably with NaBH$_4$, to form a primary alcohol —CH$_2$—OH while maintaining the multiple bond in the position 4 and 5 of the saccharide cycle. Although a person skilled in the art would expect —C=C— bond reduction in addition to the reduction of —CHO aldehyde group (or geminal diol —CH(OH)$_2$), surprisingly, the reduction of —C=C— double bond does not occur in the method according to the invention. The amount of the reduction agent can range from 0.1 to 10 equivalents, based on the repeating unit of the polysaccharide, preferably 0.3 to 2 equivalents. The reaction can be performed in water at the temperature of 5-40° C., pH 5-10, preferably at the temperature of 15-25° C. and pH 6-8 during 1-24 hrs. The concentration of the starting aldehyde solution is preferably 0.1 to 8% wt.

The above mentioned facts imply that the method of preparation of polysaccharide derivatives according to this invention requires the starting polysaccharide to include the structure Y that comprises (1→3) linked saccharide cycle, primary —$CH_2$—OH group in the position 6, and —OH, —$SO_2$—OH or —$SO_2$—ONa group in the position 4. The group in the position 2 is not crucial for successful performance of the given modification; for most of polysaccharides R is —OH or —NH—CO—$CH_3$.

Further, the invention relates to the use of polysaccharide derivatives of the general formula X. As it was mentioned above, the solution described in this invention offers new types of polysaccharide derivatives having an enhanced nucleophilicity (antioxidant properties) and at the same time only a minor change of the polysaccharide primary structure caused by elimination of hydrogen from the position 5 and —OH, —O—$SO_2$—OH or —O—$SO_2$—ONa group from the position 4. Antioxidant properties of these new derivatives were proved by standard determination with 2,2-diphenyl-1-picrylhydrazyl radical, where significant differences between polysaccharide unsaturated derivatives prepared according to the invention and saturated (non-modified) analogues were observed. That is why the derivatives according to the invention can be used for example for the preparation of materials with an antioxidant effect.

Further, it was found that if hyaluronic acid is the polysaccharide, the unsaturated derivative can be used for the preparation of a material with an anticancer effect. Biological properties of the prepared derivatives were tested on several carcinoma cell lines, and in all cases a reduced viability was observed, whereas the growth of standard fibroblasts was not suppressed within the whole range of the tested concentrations.

The term "polysaccharide" refers to a polysaccharide containing a structural unit Y, such as e.g. hyaluronic acid, carrageenan, dermatan sulfate, keratan sulfate, or chondroitin sulfate, or a pharmaceutically acceptable salt thereof.

The term "pharmaceutically acceptable salt" refers to salts that are safe and efficient for the use in vivo and have a desired biological activity. Pharmaceutically acceptable salts preferably comprise ions of alkali metals or ions of alkaline earth metals, more preferably $Na^+$, $K^+$, $Mg^+$ or $Li^+$.

The realization of the solution described in this invention is not technologically complicated and it does not require the use of expensive chemicals, solvents, or isolation procedures.

DETAILED DESCRIPTION OF THE DRAWINGS

The scheme shows the development of the growth inhibition of cancer cells MDA-MB-231—breast adenocarcinoma, A-549—lung adenocarcinoma, HEP-G2—hepatocellular carcinoma, compared to the inhibition of NHDF—primary human dermal fibroblasts.

The procedure is described in Example 27.

CS—chondroitin sulfate

ΔCS—chondroitin sulfate dehydrated in the positions 4 and 5 (Example 2) tested by means of 2,2-diphenyl-1-picrylhydrazyl (DTTH) by the procedure described in the Example 23

Statistical significance t-test—* $p<0.05$;  $p<0.01$; * $p<0.001$

Preferred Embodiments of the Invention

DS=substitution degree=100%*(molar amount of the modified saccharide unit)/(molar amount of the repeating polysaccharide unit)

The term equivalent (eq.) as used herein refers to the repeating unit of a particular polysaccharide, if not stated otherwise. The percentage is specified as weight percent if not indicated otherwise.

The molecular weight of starting polysaccharides is weight average molecular weight determined by the SEC-MALLS method.

Example 1

Oxidation and Elimination of Chondroitin Sulphate (CS) =Preparation of α,β-Unsaturated CS Aldehyde A sodium hypochlorite solution (0.8 eq., 11% of active chlorine) was gradually added into a 2% aqueous solution of CS (200 mg, Mw=$4.10^4$ g·$mol^{-1}$) cooled to 5° C. and containing di-sodium hydrogen phosphate dodecahydrate (2.2 eq.), sodium bromide (0.8 eq.), and 4-AcNH-TEMPO (0.01 eq.). The mixture was stirred for 2 hours at the temperature of 5° C. Then ethanol (10 eq.) was added to the reaction, and the reaction was stirred for another one hour at room temperature. The product was isolated by precipitation with IPA and analysed by means of NMR.

DS=23% (determined by NMR)

Example 2

Reduction of α,β-Unsaturated CS Aldehyde=Preparation of ΔCS

A 2% solution w/v of α,β-unsaturated CS aldehyde (200 mg, 0.5 mmol) in distilled water was prepared, the solution was cooled to 5° C. and then 2 equivalents of sodium borohydride were added. The reaction mixture was stirred for 4 hours at 5° C. The product was isolated by precipitation with isopropanol and analysed by means of NMR.

DS=25% (determined by NMR), Mw=$2.10^4$ g·$mol^{-1}$ (determined by SECMALLS)

Spectral analysis of ΔCS: NMR $^1H$ (500 MHz, $D_2O$, δ ppm): 2.02 and 2.04 (3H; Ac—NH—; bs); 4.03 (2H; H6; bs); 4.22 (1H; H2; bs); 4.26 (1H; H3; bs); 5.06 (1H; H1; bs); 5.18 (1H; H4; bs); NMR $^1H$-$^1H$ COSY ($D_2O$); cross peaks; δ ppm: 4.22-5.06; 4.26-5.18; NMR $^1H$-$^{13}C$ HSQC ($D_2O$); cross peaks; δ ppm: 4.03-61.0; 4.22-50.5; 4.26-73.4; 5.06-98.3; 5.18-98.9; NMR DOSY ($D_2O$); log D ((2.02 and 2.04; Ac—NH—); (4.03; H6); (4.22; H2); (4.26; H3); (5.06; H4); (5.18; H1)) ~−10.4 $m^2s^{-1}$; log D (4.72; $H_2O$) ~−8; 6 $m^2s^{-1}$; IR (KBr; $cm^{-1}$): 1660 (v —C=C— st);

Example 3

Oxidation and Elimination of Dermatan Sulfate (DeS)=Preparation of α,β-Unsaturated DeS Aldehyde An aqueous solution of sodium hypochlorite (0.8 eq., 11% of active chlorine) was gradually added into a 2% aqueous solution of DeS (200 mg, 0.42 mmol) cooled to 5° C. and containing di-sodium hydrogen phosphate dodecahydrate (2.2 eq.), sodium bromide (0.8 eq.), and 4-AcNH-TEMPO (0.01 eq.), the mixture was stirred for 2 hours at 5° C. Then ethanol (10 eq.) was added to the reaction, and the reaction was stirred for another one hour at room temperature. The product was isolated by precipitation with IPA and analysed by means of NMR.

DS=20% (determined by NMR)

Example 4

Reduction of α,β-Unsaturated Dermatan Sulfate Aldehyde=Preparation of ΔDeS

A 2% solution w/v of α,β-unsaturated DeS aldehyde (200 mg, 0.5 mmol) in distilled water was prepared. The solution was cooled to 5° C. and then sodium borohydride (2 equivalents per DeS disaccharide) were added. The reaction mixture was stirred for 4 hours at 5° C. The product was isolated by precipitation with isopropanol and analysed by means of NMR.

DS=23% (determined by NMR)

Spectra analysis of ADeS: NMR $^1$H(500 MHz, $D_2O$, δ ppm): 2.01 (3H, Ac—NH—, bs), 5.05 (1H, H1, bs), 5.17 (1H, H1, bs).

Example 5

Oxidation and Elimination of Carrageenan (KA)=Preparation of α,β-Unsaturated KA Aldehyde An aqueous solution of sodium hypochlorite (0.8 eq., 11% of active chlorine) was gradually added into a 1% aqueous solution of KA (200 mg, 0.31 mmol) cooled to 10° C., containing di-sodium hydrogen phosphate dodecahydrate (2.2 eq.), sodium bromide (0.8 eq.), and 4-AcNH-TEMPO (0.01 eq.). The mixture was stirred for 2 hours at 10° C. Then ethanol (10 eq.) was added to the reaction, and the reaction was stirred for another one hour at room temperature. The product was isolated by precipitation with IPA and analysed by means of NMR.

DS=10% (determined by NMR)

Example 6

Reduction of α,β-Unsaturated Carrageenan Aldehyde=Preparation of ΔKA

A 2% solution w/v of α,β-unsaturated KA aldehyde (200 mg, 0.5 mmol) in distilled water was prepared. The solution was cooled to 5° C. and then sodium borohydride (2 equivalents per KA disaccharide) were added. The reaction mixture was stirred for 4 hours at 5° C. The product was isolated by precipitation with isopropanol and analysed by means of NMR.

DS=13% (determined by NMR)

NMR $^1$H(500 MHz, $D_2O$, δ ppm): 5.07 (1H, H1, bs), 5.18 (1H, H1, bs),

Example 7

Oxidation of Keratan Sulfate (KS)=Preparation of KS-Aldehyde

An aqueous solution of NaClO (0.3 eq.) was gradually, under nitrogen, added into a 1% aqueous solution of KS (1 g, $2.10^4$ g·mol$^{-1}$) containing NaCl 1%, KBr 1%, TEMPO (0.01 eq.), and NaHCO$_3$ (20 eq.). The mixture was stirred for 24 h at 0° C., then 0.1 g of sodium thiosulfate was added and the mixture was stirred for further 10 minutes. The resulting solution was diluted with distilled water to 0.2% and dialyzed against the mixture of (0.1% NaCl, 0.1% NaHCO$_3$) 5 litres 3 times (once a day), and against distilled water, 5 litres 7 times (2 times a day). The resulting solution was then evaporated and analysed.

DS 3% (determined by NMR)

Example 8

Elimination of KS-Aldehyde=Preparation of α,β-Unsaturated KS Aldehyde 6.7 ml of DMSO and DIPEA base (5 eq.) were added into a 3% KS-aldehyde solution (0.1 g, oxidation degree of DS=3%, example 7) in water. The mixture was stirred for 72 hours at the temperature of 60° C. Then the resulting solution was precipitated by isopropanol/hexane mixture and the solid part was vacuum dried.

DS 2% (determined by NMR), $^1$H NMR ($D_2O$) δ 9.22 (s, 1H, —CH=O), 6.32 (m, 1H, —CH=C—CH=O)

Example 9

Reduction of α,β-Unsaturated KS Aldehyde=Preparation of ΔKS

Sodium borohydride (2 eq.) was added into a 2% solution of α,β-unsaturated KS aldehyde (200 mg, Example 8) in distilled water. The reaction mixture was stirred for 3 hours at 5° C., then precipitated with isopropanol, and analysed by NMR.

DS=2% (determined by NMR)

$^1$H NMR ($D_2O$) 5.05 (1H, H1, bs), 5.17 (1H, H4, bs)

Example 10

Oxidation of Hyaluronic Acid (HA)=Preparation of HA-Aldehyde

An aqueous solution of NaClO (0.5 eq.) was gradually, under nitrogen, added into a 1% aqueous solution of HA (1 g, $2.10^5$ g·mol$^{-1}$) containing NaCl 1%, KBr 1%, TEMPO (0.01 eq.), and NaHCO$_3$ (20 eq.). The mixture was stirred for 12 h at 0° C., then 0.5 ml of ethanol was added and the mixture was stirred for another 1 hour. The resulting solution was diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 10% (determined by NMR)

Example 11

Oxidation of HA=Preparation of HA-Aldehyde

An aqueous solution of NaClO (0.5 eq.) was gradually, under nitrogen, added into a 1% aqueous solution of HA (1 g, $2.10^5$ g·mol$^{-1}$) containing NaCl 1%, KBr 1%, N-acetylamino-TEMPO (0.01 eq.), and NaHCO$_3$ (20 eq.). The mixture was stirred for 12 h at 10° C., then 0.1 ml of ethanol was added and the mixture was stirred for another 1 hour. The resulting solution was diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 9% (determined by NMR)

Example 12

Oxidation of HA=Preparation of HA-Aldehyde

An aqueous solution of NaClO (0.3 eq.) was gradually, under nitrogen, added into a 1% aqueous solution of HA (1 g, 2.10$^5$ g·mol$^{-1}$) containing NaCl 1%, KBr 1%, TEMPO (0.2 eq.), and NaHCO$_3$ (20 eq.). The mixture was stirred for 48 h at 5° C., then 0.1 ml of ethanol was added and the mixture was stirred for another 1 hour. The resulting solution was diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 5% (determined by NMR)

Example 13

Oxidation of Hyaluronic Acid (HA)=Preparation of HA-Aldehyde

An aqueous solution of NaClO (0.7 eq.) was gradually, under nitrogen, added into a 1% aqueous solution of HA (1 g, 2.10$^5$ g·mol$^{-1}$) containing NaCl 1%, KBr 1%, TEMPO (0.01 eq.), and NaHCO$_3$ (20 eq.). The mixture was stirred for 0.5 h at 0° C., then 0.1 ml of ethanol was added and the mixture was stirred for another 1 hour. The resulting solution was diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 9% (determined by NMR)

Example 14

Oxidation of Hyaluronic Acid (HA)=Preparation of HA-Aldehyde

An aqueous solution of NaClO (0.5 eq.) was gradually, under nitrogen, added into 1% aqueous solution of HA (1 g, 2.10$^5$ g·mol$^{-1}$) containing NaCl 1%, KBr 1%, TEMPO (0.01 eq.), and NaHCO$_3$ (20 eq.). The mixture was stirred for 12 h at 0° C., then 0.1 ml of ethanol was added and the mixture was stirred for another 1 hour. The resulting solution was diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 10% (determined by NMR)

Example 15

Oxidation of Hyaluronic Acid (HA)=Preparation of HA-Aldehyde 1.2 eq. of 1,1,1-triacetoxy-1,1-dihydro-1,2-benziodoxol-3 (1H)-one (Dess-Martin Periodinan) was added into a 1% solution of acid form of hyaluronane (1 g, 1.10$^5$ g·mol$^{-1}$) in non-aqueous DMSO, and the mixture was stirred for 5 h at 20° C. The resulting solution was then diluted with distilled water to 0.2% and dialyzed against the mixture of (0.1% NaCl, 0.1% NaHCO$_3$), 5 litres 3 times (once a day), and against distilled water, 5 litres 7 times (2 times a day). Then the resulting solution was evaporated and analysed.

DS 40% (determined by NMR)

Example 16

Elimination of HA-Aldehyde=Preparation of α,β-Unsaturated HA Aldehyde 6.7 ml of DMSO and DIPEA base (5 eq.) were added into a 3% solution of HA-aldehyde (0.1 g, oxidation degree DS=40%, Example 15) in water. The mixture was stirred for 72 hours at 60° C. The resulting solution was then precipitated by isopropanol/hexane mixture and the solid part was vacuum dried.

DS 20% (determined by NMR), $^1$H NMR (D$_2$O) δ 9.24 (s, 1H, —CH=O), 6.32 (m, 1H, —CH=C—CH=O)

UV-Vis (D$_2$O) 252 nm, π-π* transition α,β-unsaturated aldehyde

Example 17

Elimination of HA-Aldehyde=Preparation of 4-Unsaturated HA Aldehyde 6.7 ml of DMSO and triethylamine base (20 eq.) were added into a 3% solution of HA-aldehyde (0.1 g, oxidation degree DS=10%, Example 10) in water. The mixture was stirred for 150 hours at 30° C. The resulting solution was then precipitated by isopropanol/hexane mixture and the solid part was vacuum dried.

DS 5% (determined by NMR)

Example 18

Elimination of HA-Aldehyde=Preparation of 4-Unsaturated HA Aldehyde 6.7 ml of DMSO and pyridine base (0.01 eq.) were added into a 3% solution of HA-aldehyde (0.1 g, oxidation degree DS=10%, Example 10) in water. The mixture was stirred for 12 hours at 80° C. The resulting solution was then precipitated by isopropanol/hexane mixture and the solid part was vacuum dried.

DS 3% (determined by NMR)

Example 19

Elimination of HA-Aldehyde=Preparation of α,β-Unsaturated HA Aldehyde 1.7 ml of DMSO and pyridine base (10 eq.) were added into a 3% solution of HA-aldehyde (0.1 g, oxidation degree DS=10%, Example 10) in water. The mixture was stirred for 48 hours at 60° C. The resulting solution was then precipitated by isopropanol/hexane mixture and the solid part was vacuum dried.

DS 4% (determined by NMR)

Example 20

Elimination of HA-Aldehyde=Preparation of α,β-Unsaturated HA Aldehyde 10 ml of DMSO and DIPEA base (5 eq.) were added into a 3% solution of HA-aldehyde (0.1 g, oxidation degree DS=10%, Example 10) in water. The mixture was stirred for 48 hours at 60° C. The resulting solution was then precipitated by isopropanol/hexane mixture and the solid part was vacuum dried.

DS 5% (determined by NMR)

Example 21

Elimination of HA-Aldehyde=Preparation of α,β-Unsaturated HA Aldehyde 6.7 ml sulfonane and DIPEA base (5 eq.) were added into a 3% solution of HA-aldehyde (0.1 g, oxidation degree DS=10%, Example 10) in water. The mixture was stirred for 72 hours at 50° C. The resulting solution was then precipitated by isopropanol/hexane mixture and the solid portion was vacuum dried.

DS 5% (determined by NMR)

Example 22

Reduction of α,β-Unsaturated HA Aldehyde=Preparation of ΔHA

Sodium borohydride (10 eq.) was added into a 2% solution of α,β-unsaturated HA aldehyde (200 mg, Example 16) in distilled water, at 5° C. The reaction mixture was stirred for 1 h at 5° C., then precipitated with isopropanol and analysed by NMR.

DS 20% (determined by NMR)

$^1$H NMR (D$_2$O) 5.06 (1H, H1, bs), 5.17 (1H, H1, bs)

Example 23

Reduction of α,β-Unsaturated HA Aldehyde=Preparation of ΔHA

Sodium borohydride (0.1 eq.) was added into a 2% solution of α,β-unsaturated HA aldehyde (200 mg, Example 17) in distilled water, at 5° C. The reaction mixture was stirred for 20 h at 5° C., then precipitated with isopropanol and analysed by NMR.

DS=4% (determined by NMR)

Example 24

Reduction of α,β-Unsaturated HA Aldehyde=Preparation of ΔHA

Sodium borohydride (1 eq.) was added into a 2% solution of α,β-unsaturated HA aldehyde (200 mg, Example 17) in distilled water, at 40° C. The reaction mixture was stirred for 1 h at 40° C., then precipitated with isopropanol and analysed by NMR.

DS=5% (determined by NMR)

Example 25

Reduction of α,β-Unsaturated HA Aldehyde=Preparation of ΔHA

Sodium borohydride (2 eq.) was added into a 2% solution of α,β-unsaturated HA aldehyde (200 mg, Example 17) in distilled water, at 20° C. The reaction mixture was stirred for 4 h at 20° C., then precipitated with isopropanol and analysed by NMR.

DS=5% (determined by NMR)

Example 26

Figure 2:
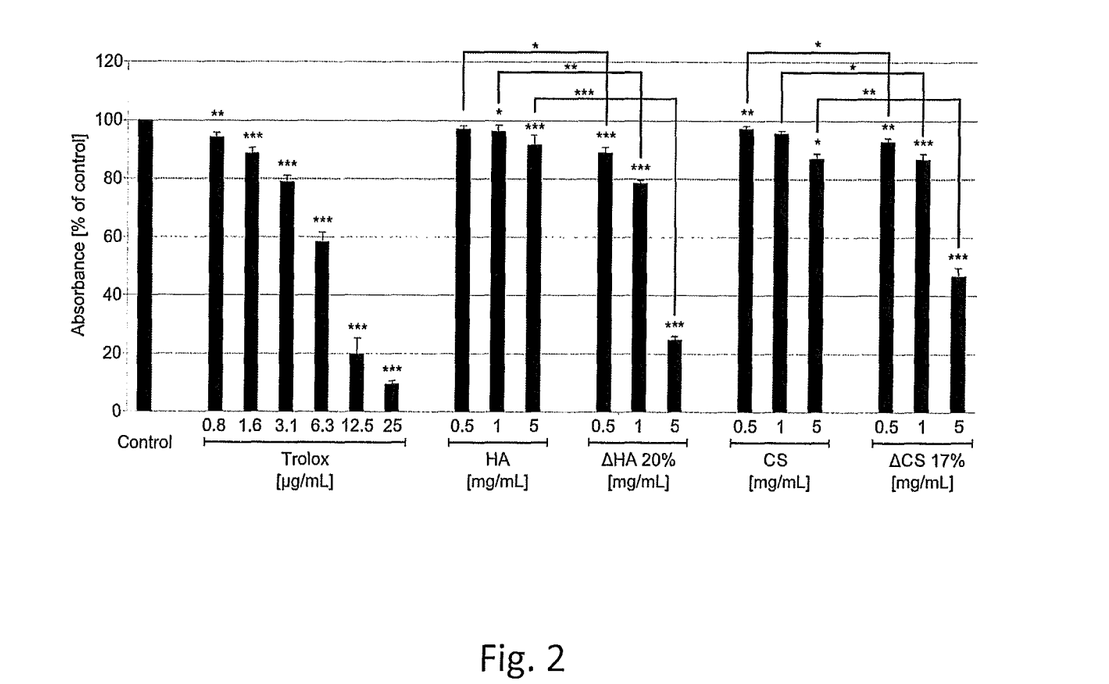
FIG. 2—antioxidant properties of ΔHA and ΔCS materials compared to the non-modified polysaccharides HA, CS, and to the standard—Trolox—6-hydroxy-2,5,7,8-tetramethylchromane-2-carboxylic acid HA—hyaluronic acid ΔHA—hyaluronic acid dehydrated in the positions 4 and 5 (Example 22)

Determination of Oxidation Activity (FIG. 2)

An antioxidative activity of ΔHA polysaccharides prepared according to the Example 22 and ΔCS prepared according to the Example 2 was determined by means of a stable free radical 2,2-diphenyl-1-picrylhydrazyl (DPPH). This determination was performed according to the description in (Brand-Williams W. et al., *LWT—Food Science and Technology*, 28, 1, 25-30, 1995), with a minor modification. Briefly, 100 μL of 0.01% DPPH solution in methanol were added into 100 μL of the tested substance dissolved in 50 mM of Tris pH 7.1. The decrease of the absorbance was measured after 15 min at 515 nm. Trolox (6-hydroxy-2,5,7,8-tetramethylchromane-2-carboxylic acid) was used as the positive control. Data were measured in three independent experiments. T-test was used for the evaluation of the statistical significance * p<0.05,  p<0.01, * p<0.001 (FIG. 2).

Example 27

Figure 1:
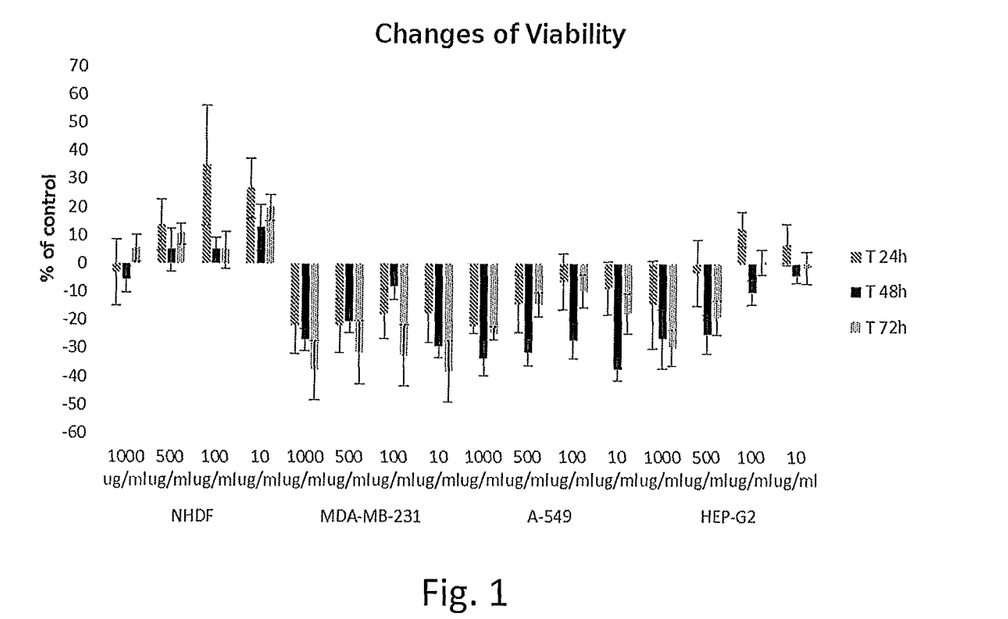
FIG. 1—Effect of ΔHA prepared according to Example 25 on cells viability

Testing of Cytotoxicity of the Derivatives Prepared According to the Example 25 (FIG. 1)

A cytotoxicity effect of the HA derivative was compared for non-cancer cells—primary human dermal fibroblasts, and for breast carcinoma cell lines (MDA-MB-231), lung carcinoma cell lines (A-549), and hepatocellular carcinoma cell lines (HEP-G2). For the purpose of the experiments, the cells were cultured under standard conditions (37° C., 5% CO$_2$) in a proper medium (10% FBS—fetal bovine serum). After achieving an 80% confluency, the cells were passaged, counted by means of an automatic counter CASY TT, Roche, and put on 96-wells panels at the density of 5,000 cells per well in 200 μl of media. After 24 hours, the medium was replaced with the solutions of the tested substances of concentrations of 1,000; 500; 100; and 10 μg/mL of 10% medium. The cell viability was measured 24, 48, and 72 hours after the treatment by means of MTT test—20 μL of MTT solution (5 mg/mL) was added into each well, followed by an incubation for 2.5 hours and cell lysis with solubilisation solution (IPA:DMSO 1:1 s 10% Triton X-100 and 9.9% 37% HCl) for 30 minutes. Then the absorbance was measured by means of Microplate reader VERSAmax at 570 nm and 690 nm (background correction). The viability of the treated cells was evaluated by correlation with untreated control that corresponds to zero in FIG. 1. The values above zero refer to a cell activation (no cytotoxic effect of the derivatives) and the values below zero indicate a reduced cell viability—i.e. the cytotoxic effect of the derivatives. In case of NHDF, it is obvious, in FIG. 1, that the tested derivative had no cytotoxic effect. In case of the carcinoma lines (MDA-MB-231, A-549, HEP-G2) a cytotoxic effect of the derivatives was observed. Based on the results of the presented tests, a potential anti-cancer effect of the derivative can be deduced (FIG. 1).

The invention claimed is:

1. Unsaturated derivatives of polysaccharides comprising, in their structure, at least one heterocycle having a double bond in positions 4 and 5 according to the structural formula X, where R represents —NH—CO—CH$_3$ or —OH.

2. Unsaturated derivatives of polysaccharides according to claim 1 characterized in that their molecular weight is in the range of $5.10^3$ to $5.10^5$ g·mol$^{-1}$ and that the polysaccharides are selected from the group consisting of chondroitin sulfate, carrageenan, dermatan sulfate, hyaluronic acid, and keratan sulfate.

3. A method of preparation of the polysaccharide derivatives defined in claim 1 characterized in that the starting polysaccharide, comprising the fragment Y where R is —NH—CO—CH$_3$ or —OH, and R$^1$ is —SO$_2$—ONa, —SO$_2$—OH or —H, is in the first step oxidized to an aldehyde in the position 6, in the second step the oxidized polysaccharide is eliminated in the positions 4 and 5 of the cycle to form a double bond, and in the third step the aldehyde group is selectively reduced.

4. The method of preparation according to claim 3 characterized in that the starting polysaccharide is chondroitin sulfate, carrageenan, dermatan sulfate, hyaluronic acid, or keratan sulfate.

5. The method of preparation according to claim 3 characterized in that, in the first step, the oxidation in the position C-6 proceeds either by means of the R$^3$-TEMPO/NaClO system, where R$^3$ is hydrogen or N-acetyl group, in water at the temperature of 0° C. to 10° C., wherein the molar amount of NaClO is within the range of 0.3 to 0.8 eq. and the molar amount of R$^3$-TEMPO is within the range of 0.005 to 0.2 eq., with respect to the repeating unit of the polysaccharide, or by means of 1,1,1-triacetoxy-1,1-dihydro-1,2-benziodoxol-3(1H)-one (DMP) in DMSO at the temperature of 10° C. to 50° C., wherein the amount of DMP is within the range of 0.05 to 2 eq., with respect to the repeating unit of the polysaccharide.

6. The method of preparation according to claim 3 characterized in that the starting polysaccharide is hyaluronic acid or keratan sulfate, and that, in the second step, the oxidized polysaccharide undergoes the elimination reaction in a mixture of water/polar aprotic solvent in the presence of a base at the temperature of 30 to 80° C.

7. The method of preparation according to claim 6 characterized in that the amount of the base is 5 to 10 eq., with respect to the repeating polysaccharide unit, wherein the base is selected from the group consisting of pyridine, triethylamine, N,N-diisopropylethylamine, and Ca(OH)$_2$.

8. The method of preparation according to claim 6 characterized in that the aprotic solvent is water miscible and comprises DMSO or sulfolane, and the volume ratio of solvent/water is in the range of 3/1 to 1/2.

9. The method of preparation according to claim 6 characterized in that the second reaction step proceeds for 12 to 150 hours.

10. The method of preparation according to claim 3 characterized in that the starting polysaccharide is chondroitin sulfate, carrageenan, or dermatan sulfate, and that the oxidized polysaccharide is spontaneously eliminated in the second step directly in the reaction mixture to form an α,β-unsaturated aldehyde.

11. The method of preparation according to claim 3 characterized in that the molecular weight of the starting polysaccharide is in the range of $5.10^3$ to $5.10^5$ g·mol$^{-1}$.

12. The method of preparation according to claim 3 characterized in that sodium borohydride is added in the third step in the amount of 0.1 to 10 equivalents, calculated with respect to the repeating polysaccharide unit, in water, at the temperature of 5-40° C., at the pH in the range of 5 to 10.

13. The method of preparation according to claim 3 characterized in that the starting polysaccharide is hyaluronic acid or keratan sulfate, and that, in the second step, the oxidized polysaccharide undergoes the elimination reaction in a mixture of water/polar aprotic solvent in the presence of a base at a temperature of 50° C. to 60° C.

14. The method of preparation according to claim 6 characterized in that the amount of the base is 0.01 to 20 eq., with respect to the repeating polysaccharide unit.

15. The method of preparation according to claim 3 characterized in that sodium borohydride is added in the third step in the amount of 0.3 to 2 equivalents, calculated with respect to the repeating polysaccharide unit, in water, at a temperature of 15-25° C., at a pH in the range of 6 to 8.

* * * * *

UNITED STATES PATENT AND TRADEMARK OFFICE
CERTIFICATE OF CORRECTION

PATENT NO. : 10,618,984 B2
APPLICATION NO. : 16/311745
DATED : April 14, 2020
INVENTOR(S) : Radovan Buffa et al.

Page 1 of 1

It is certified that error appears in the above-identified patent and that said Letters Patent is hereby corrected as shown below:

On the Title Page

Column 1, Page 6, item (56) Line 71, "trough" should be --through--.

Column 1, Page 7, item (56) Line 63, "angineering," should be --engineering,--.

In the Specification

Column 8, Line 27, "weight average molecular weight" should be --average molecular weight--.

Signed and Sealed this
Twenty-third Day of June, 2020

Andrei Iancu
*Director of the United States Patent and Trademark Office*